(12) United States Patent
Bierman

(10) Patent No.: US 8,057,440 B2
(45) Date of Patent: Nov. 15, 2011

(54) ANCHORING SYSTEM FOR USE WITH NEONATES

(75) Inventor: Steve F. Bierman, Del Mar, CA (US)

(73) Assignee: Venectec International, Inc., Covington, GA (US)

( * ) Notice: Subject to any disclaimer, the term of this patent is extended or adjusted under 35 U.S.C. 154(b) by 224 days.

(21) Appl. No.: 11/442,701

(22) Filed: May 26, 2006

(65) Prior Publication Data

US 2006/0270995 A1 Nov. 30, 2006

Related U.S. Application Data

(60) Provisional application No. 60/685,182, filed on May 26, 2005.

(51) Int. Cl.
*A61M 5/32* (2006.01)

(52) U.S. Cl. ........................................ 604/180; 604/174

(58) Field of Classification Search .................. 604/174, 604/177, 178, 180, 513, 533; 128/DIG. 6, 128/DIG. 26, 877–879

See application file for complete search history.

(56) References Cited

U.S. PATENT DOCUMENTS

| | | | |
|---|---|---|---|
| 3,046,984 A | 7/1962 | Eby | |
| 3,167,072 A * | 1/1965 | Stone et al. | 604/179 |
| 3,194,235 A | 7/1965 | Cooke | |
| 3,288,137 A * | 11/1966 | Lund | 604/180 |
| 3,630,195 A | 12/1971 | Santomieri | |
| 3,826,254 A | 7/1974 | Mellor | |
| 3,900,026 A * | 8/1975 | Wagner | 128/888 |
| 3,901,226 A | 8/1975 | Scardenzan | |
| 4,082,094 A | 4/1978 | Dailey | |
| 4,129,128 A | 12/1978 | McFarlane | |
| D252,822 S | 9/1979 | McFarlane | |
| 4,193,174 A | 3/1980 | Stephens | |
| 4,224,937 A | 9/1980 | Gordon | |
| 4,250,880 A | 2/1981 | Gordon | |

(Continued)

FOREIGN PATENT DOCUMENTS

CA 1 311 977 12/1992

(Continued)

OTHER PUBLICATIONS

U.S. Appl. No. 09/136,271, applicant Steven F. Bierman, filed Aug. 18, 1998.

*Primary Examiner* — Kevin C Sirmons
*Assistant Examiner* — Emily Schmidt
(74) *Attorney, Agent, or Firm* — Knobbe Martens Olson & Bear LLP

(57) ABSTRACT

A catheter securement device holds a medical article by securing an anchor member to an attachment region of a neonate. The attachment region is located on the body of the neonate. The catheter securement device defines a central channel into which at least a portion of the medical article is inserted. The catheter securement device includes at least one mounting wing and a body member. The mounting wing contacts the anchor member over the attachment region and lifts the medical article away from the neonate's skin. At least a portion of the body member is located in a distal direction from the attachment region and does not directly contact the neonate's skin. A soft material may be inserted between the distal portion of the body member and the neonate's skin to further inhibit rocking of the medical article upon the neonate.

24 Claims, 18 Drawing Sheets

U.S. PATENT DOCUMENTS

| | | |
|---|---|---|
| 4,333,468 A | 6/1982 | Geist |
| 4,470,410 A | 9/1984 | Elliott |
| 4,484,913 A | 11/1984 | Swauger |
| 4,516,968 A | 5/1985 | Marshall et al. |
| 4,517,971 A * | 5/1985 | Sorbonne ................. 128/879 |
| 4,563,177 A | 1/1986 | Kamen |
| 4,632,670 A | 12/1986 | Muller |
| 4,633,863 A | 1/1987 | Filips et al. |
| 4,645,492 A | 2/1987 | Weeks |
| 4,669,458 A | 6/1987 | Abraham et al. |
| 4,711,636 A | 12/1987 | Bierman |
| 4,737,143 A | 4/1988 | Russell |
| 4,846,807 A | 7/1989 | Safadago |
| 4,852,844 A | 8/1989 | Villaveces |
| 4,863,432 A | 9/1989 | Kvalo |
| 4,898,587 A | 2/1990 | Mera |
| 4,976,698 A | 12/1990 | Stokley |
| 4,981,475 A | 1/1991 | Haindl |
| 4,997,421 A | 3/1991 | Palsrok et al. |
| 5,037,397 A | 8/1991 | Kalt et al. |
| 5,074,847 A | 12/1991 | Greenwell et al. |
| 5,084,026 A | 1/1992 | Shapiro |
| 5,112,313 A | 5/1992 | Sallee |
| 5,116,324 A | 5/1992 | Brierley et al. |
| 5,137,519 A | 8/1992 | Littrell et al. |
| 5,167,630 A * | 12/1992 | Paul ......................... 604/179 |
| 5,192,273 A | 3/1993 | Bierman |
| 5,192,274 A | 3/1993 | Bierman |
| 5,215,532 A | 6/1993 | Atkinson |
| 5,238,010 A | 8/1993 | Grabenkort |
| 5,290,248 A | 3/1994 | Bierman et al. |
| D347,060 S | 5/1994 | Bierman |
| 5,314,411 A | 5/1994 | Bierman et al. |
| 5,328,487 A | 7/1994 | Starchevich |
| 5,354,282 A | 10/1994 | Bierman |
| 5,356,391 A | 10/1994 | Stewart |
| 5,370,627 A | 12/1994 | Conway |
| 5,395,344 A | 3/1995 | Beisang et al. |
| 5,413,120 A | 5/1995 | Grant |
| 5,413,562 A | 5/1995 | Swauger |
| D359,120 S | 6/1995 | Sallee et al. |
| 5,456,671 A | 10/1995 | Bierman |
| D364,922 S | 12/1995 | Bierman |
| D375,355 S | 11/1996 | Bierman |
| D375,356 S | 11/1996 | Bierman |
| 5,577,516 A | 11/1996 | Schaeffer |
| 5,578,013 A | 11/1996 | Bierman |
| D377,831 S | 2/1997 | Bierman |
| 5,605,546 A | 2/1997 | Wolzinger et al. |
| 5,664,581 A | 9/1997 | Ashley |
| 5,681,290 A | 10/1997 | Alexander |
| 5,685,859 A | 11/1997 | Kornerup |
| 5,686,096 A | 11/1997 | Khan et al. |
| 5,690,616 A | 11/1997 | Mogg |
| 5,693,032 A | 12/1997 | Bierman |
| 5,702,371 A | 12/1997 | Bierman |
| 5,722,959 A | 3/1998 | Bierman |
| 5,728,053 A | 3/1998 | Calvert |
| 5,800,402 A | 9/1998 | Bierman |
| 5,800,410 A | 9/1998 | Gawreluk |
| 5,810,781 A | 9/1998 | Bierman |
| D399,954 S | 10/1998 | Bierman |
| 5,827,230 A | 10/1998 | Bierman |
| 5,827,239 A | 10/1998 | Dillon et al. |
| 5,833,666 A | 11/1998 | Davis et al. |
| 5,833,667 A | 11/1998 | Bierman |
| 5,855,591 A | 1/1999 | Bierman |
| 5,885,254 A | 3/1999 | Matyas |
| 5,897,519 A | 4/1999 | Shesol et al. |
| 6,050,934 A | 4/2000 | Mikhail et al. |
| D425,619 S | 5/2000 | Bierman |
| 6,099,509 A | 8/2000 | Brown et al. |
| 6,113,577 A | 9/2000 | Hakky et al. |
| 6,132,398 A | 10/2000 | Bierman |
| 6,132,399 A | 10/2000 | Shultz |
| 6,213,979 B1 | 4/2001 | Bierman |
| 6,224,571 B1 | 5/2001 | Bierman |
| 6,231,547 B1 | 5/2001 | O'Hara |
| 6,231,548 B1 | 5/2001 | Bassett |
| 6,258,066 B1 | 6/2001 | Urich |
| 6,283,945 B1 | 9/2001 | Bierman |
| 6,290,676 B1 | 9/2001 | Bierman |
| 6,361,523 B1 | 3/2002 | Bierman |
| 6,375,639 B1 | 4/2002 | Duplessie |
| 6,413,240 B1 | 7/2002 | Bierman et al. |
| 6,428,515 B1 | 8/2002 | Bierman et al. |
| 6,428,516 B1 | 8/2002 | Bierman |
| 6,436,073 B1 | 8/2002 | Teichert |
| 6,447,485 B2 | 9/2002 | Bierman |
| 6,447,486 B1 | 9/2002 | Tollini |
| 6,471,676 B1 | 10/2002 | DeLegge et al. |
| 6,482,183 B1 | 11/2002 | Pausch |
| 6,491,664 B2 | 12/2002 | Bierman |
| 6,500,154 B1 | 12/2002 | Hakky et al. |
| D469,530 S | 1/2003 | Gomez |
| D470,936 S | 2/2003 | Bierman |
| 6,517,522 B1 | 2/2003 | Bell et al. |
| 6,551,285 B1 | 4/2003 | Bierman |
| 6,572,588 B1 | 6/2003 | Bierman et al. |
| 6,582,403 B1 | 6/2003 | Bierman et al. |
| 6,616,635 B1 | 9/2003 | Bell et al. |
| 6,626,890 B2 | 9/2003 | Nguyen et al. |
| 6,652,487 B1 | 11/2003 | Cook |
| 6,663,600 B2 | 12/2003 | Bierman et al. |
| 6,689,104 B2 | 2/2004 | Bierman |
| D491,411 S | 6/2004 | Bierman |
| D492,411 S | 6/2004 | Bierman |
| 6,770,055 B2 | 8/2004 | Bierman et al. |
| 6,786,892 B2 | 9/2004 | Bierman |
| 6,809,230 B2 | 10/2004 | Hancock et al. |
| 6,827,705 B2 | 12/2004 | Bierman |
| 6,827,706 B2 | 12/2004 | Tollini |
| 6,827,707 B2 | 12/2004 | Wright et al. |
| 6,834,652 B2 | 12/2004 | Altman |
| 6,837,875 B1 | 1/2005 | Bierman |
| 6,866,652 B2 | 3/2005 | Bierman |
| D503,977 S | 4/2005 | Bierman |
| 6,951,550 B2 | 10/2005 | Bierman |
| 6,972,003 B2 | 12/2005 | Bierman et al. |
| 6,979,320 B2 | 12/2005 | Bierman |
| 6,981,969 B2 | 1/2006 | Chavez et al. |
| 7,014,627 B2 | 3/2006 | Bierman |
| 7,018,362 B2 | 3/2006 | Bierman et al. |
| 7,070,580 B2 | 7/2006 | Nielsen |
| 7,090,660 B2 | 8/2006 | Roberts et al. |
| D528,206 S | 9/2006 | Bierman |
| 7,153,291 B2 | 12/2006 | Bierman |
| 7,354,421 B2 | 4/2008 | Bierman |
| 2002/0068904 A1 | 6/2002 | Bierman et al. |
| 2002/0099360 A1 | 7/2002 | Bierman |
| 2002/0133121 A1 * | 9/2002 | Bierman ...................... 604/174 |
| 2003/0055382 A1 | 3/2003 | Schaeffer |
| 2003/0229313 A1 | 12/2003 | Bierman |
| 2004/0102736 A1 | 5/2004 | Bierman |
| 2004/0111067 A1 | 6/2004 | Kirchhofer |
| 2004/0138624 A1 | 7/2004 | Bierman |
| 2004/0204685 A1 | 10/2004 | Wright et al. |
| 2005/0182367 A1 | 8/2005 | Walborn |
| 2005/0215953 A1 | 9/2005 | Rossen |
| 2005/0288635 A1 | 12/2005 | Davis et al. |
| 2006/0015076 A1 | 1/2006 | Heinzerling et al. |
| 2006/0064063 A1 | 3/2006 | Bierman |
| 2006/0135944 A1 | 6/2006 | Bierman |
| 2006/0184127 A1 | 8/2006 | Bierman |
| 2006/0184129 A1 | 8/2006 | Bierman |
| 2006/0217669 A1 | 9/2006 | Botha |
| 2006/0247577 A1 | 11/2006 | Wright |
| 2006/0264836 A1 | 11/2006 | Bierman |
| 2006/0270995 A1 | 11/2006 | Bierman |

FOREIGN PATENT DOCUMENTS

| | | |
|---|---|---|
| CA | 1 318 824 | 6/1993 |
| EP | 0356683 | 3/2000 |
| FR | 2 922 458 A1 | 4/2009 |
| WO | WO 94/21319 | 9/1994 |
| WO | WO 97/15337 | 5/1997 |
| WO | WO 99/55409 | 11/1999 |
| WO | WO 2004016309 A2 * | 2/2004 |

* cited by examiner

ANCHORING SYSTEM FOR USE WITH NEONATES

RELATED APPLICATIONS

This application claims priority under 35 U.S.C. §119(e) to U.S. Provisional Patent Application Ser. No. 60/685,182, filed May 26, 2005, and which is hereby expressly incorporated by reference in its entirety.

BACKGROUND OF THE INVENTION

1. Field of the Invention

This invention relates to a securement system used to attach a medical line to a premature baby's or neonate's skin.

2. Description of the Related Art

It is common in the treatment of patients for healthcare providers to utilize catheters to introduce fluids and medications directly into the patient or to withdraw fluids from the patient. Premature babies usually require assistance to breathe and eat, and thus, are often fully instrumented. These babies also are usually fed intravenously by an intravenous (IV) catheter inserted into a vein, usually on the dorsal side of the neonate's hand or forearm. An arterial catheter may also be inserted on the ventral side of the neonate's hand for purposes of monitoring blood oxygenation.

Premature babies' present additional challenges to healthcare personnel since premature babies have less skin surface area available for attachment of a catheter. For premature babies, each catheter is precisely positioned, and the position of such is fixed relative to the neonate to prevent migration or dislodgment. Healthcare personnel usually secure the (IV) and arterial catheters using tape (and sometimes using sutures). The catheters remain in place for several days or weeks, and often require repositioning and/or replacement on a periodic basis.

Securing a catheter with tape upon the patient traditionally has certain drawbacks. The use of tape at the insertion site can retain dirt or other contaminant particles, potentially leading to infection of the neonate. Tape also fails to limit catheter motion and, therefore, contributes to motion related complications like phlebitis, infiltration and catheter migration.

Taped dressings also require periodic changes. The frequent, often daily, removal and reapplication of adhesive tape to the skin of the patient can exfoliate the upper layers of the neonate's skin in the area around the dressing. Such exfoliation of the upper layers of skin can lead to abrasions on the neonate's skin because the neonate's skin is so thin, sensitive and fragile. Moreover, infection and disease can occur as a result of such skin wounds owing to the relatively undeveloped nature of a neonate's immune system.

Such repeated applications of tape over the catheter or medical line can additionally lead to the build up of adhesive residue on the outer surface of the catheter or medical line. This residue can result in contaminants adhering to the catheter itself, increasing the likelihood of infection of the insertion site. This residue can also make the catheter or medical line stickier and more difficult to handle for healthcare providers.

Catheter systems have been developed for neonate applications. Even though the limited skin surface area of a premature baby may warrant the use of a reduced or miniature sized catheter, the use of such small catheters would import additional difficulties for healthcare personnel during the treatment of the premature baby. Thus, catheter manufacturers often size their catheters to facilitate handling and manipulation by healthcare personnel.

The attachment region on a catheter retention device may be larger than the available skin surface of a neonate. Further, when the tip of the catheter is aligned with the insertion site on a neonate, the body of the catheter may extend beyond the available skin surface. Due to the relative size difference between the available skin surface of a neonate and the length of the catheter, these systems tend to be relatively large and may result in the skin attachment location of the catheter retention device being located at an undesirable distance from the insertion site.

SUMMARY OF THE INVENTION

The systems and methods of the present invention have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description of the Preferred Embodiments," one will understand how the features of this invention provide several advantages over traditional catheter securement techniques.

An aspect of the present invention involves a securement device for anchoring a medical article to a patient's skin. The securement device comprises at least one anchor member that has a lower adhesive surface configured to attach to skin of a patient and a retainer. The retainer comprises a body member that has a channel formed therethrough about a channel axis and that terminates at a proximal end of the body member. The channel retains at least a portion of the medical article and has a longitudinal access opening to allow at least ingress of the portion of the medical article into the channel. The retainer further comprises at least one abutment that extends generally normal to the channel axis so as to inhibit longitudinal movement of the retained portion of the medical article relative to the body member. The retainer further comprises at least one mounting wing that supports the body member and has an attachment portion mounted on the anchor member. The attachment portion is disposed entirely to one side of and beyond the proximal end of the body member.

Another aspect of the present invention involves a securement device for anchoring a medical article to a patient's skin. The securement device comprises one or more anchor members having a lower adhesive surface configured to attach to skin of a patient and a retainer. The retainer comprises a body member that has a channel formed therethrough about a channel axis. The channel retains at least a portion of the medical article and has a longitudinal access opening to allow at least ingress of the portion of the medical article into the channel. The retainer further comprises at least one abutment that extends generally normal to the channel axis so as to inhibit longitudinal movement of the retained portion of the medical article relative to the body member. The retainer further comprises at least a pair of mounting wings that support the body member. Each mounting wing has an attachment portion mounted on the one or more anchor members. The attachment portions are spaced apart from each other to define an insertion side space. The mounting wings together support the body member at a position distal of the insertion side space.

An additional aspect of the present invention involves a securement device for anchoring a medical article to a patient's skin. The securement device comprises at least one anchor member that has a lower adhesive surface configured to attach to skin of a patient and a retainer. The retainer comprises a body member that has a channel formed therethrough about a channel axis. The channel retains at least a portion of the medical article and has a longitudinal access opening to allow at least ingress of the portion of the medical article into the channel. The channel has a longitudinal midpoint. The retainer further comprises at least one support disposed to a side of the channel axis and that has an attachment portion mounted on the anchor member. The attachment portion has a longitudinal midpoint that is offset from the longitudinal midpoint of the channel along a longitudinal axis.

Another aspect of the present invention involves a securement device for anchoring a medical article to a patient's skin. The securement device comprises at least one anchor member that has a lower adhesive surface configured to attach to skin of a patient and a retainer. The retainer comprises a body member that has a channel formed therethrough about a channel axis. The channel retains at least a portion of the medical article and has a longitudinal access opening to allow at least ingress of the portion of the medical article into the channel. The channel has a longitudinal midpoint. The retainer further comprises at least one support that is mounted on the anchor member. The body member is cantilevered from the support so as to suspend the body member off the body of the patient.

Another aspect of the present invention involves a securement device for anchoring a medical article to a patient's skin. The securement device comprises an anchor member and a retainer. The retainer comprises a body member that includes a channel formed therethrough. The channel retains a portion of the medical article and has a longitudinal access opening disposed on an underside of the body member to allow ingress of the medical article into the channel. The retainer further comprises at least one abutment that extends generally normal to an axis of the channel to inhibit longitudinal movement of the medical article. The retainer further comprises at least one mounting wing that supports the body and has an attachment portion mounted to the anchor member. An overall longitudinal length of the at least one mounting wing exceeds the longitudinal length of the attachment portion.

Another aspect of the present invention involves a method of securing a medical article to a skin surface of a patient. The method comprises providing a medical article, selecting an attachment region on the surface of the patient for inserting the medical article, and providing a retainer having a channel formed therethrough and at least one abutment. The channel is disposed to a distal side of the retainer to receive and retain the medical article. The at least one abutment extends generally normal to the channel. The method further comprises positioning the retainer on the medical article, pressing the medical article into the channel through an opening formed on the underside of the retainer, and abutting the medical article against the abutment to inhibit longitudinal motion of the medical article relative to the retainer in at least one direction. The method further comprises aligning an attachment portion of the retainer with the attachment region on the patient so that a substantial portion of the channel is located outside of the attachment region and adhering the retainer to at least the attachment region on the patient.

BRIEF DESCRIPTION OF THE DRAWINGS

These and other features, aspects, and advantages of the present invention will now be described in connection with preferred embodiments of the invention, in reference to the accompanying drawings. The illustrated embodiments, however, are merely examples and are not intended to limit the invention.

DETAILED DESCRIPTION OF THE PREFERRED EMBODIMENTS

The following description and the accompanying figures, which describe and show preferred embodiments, are made to demonstrate several possible configurations that a securement system can take to include various aspects and features.

The illustrated embodiments are shown in use with an exemplary catheter hub. The illustration of the securement system in this context is not intended to limit the disclosed aspects and features to the specified embodiments or to usage only with the illustrated hub. Those of skill in the art will recognize that the disclosed aspects and features are not limited to any particular embodiment of a securement system, and securement systems, which include one or more of the inventive aspects and features herein described, can be designed for use with a variety of medical articles.

Figure 1:
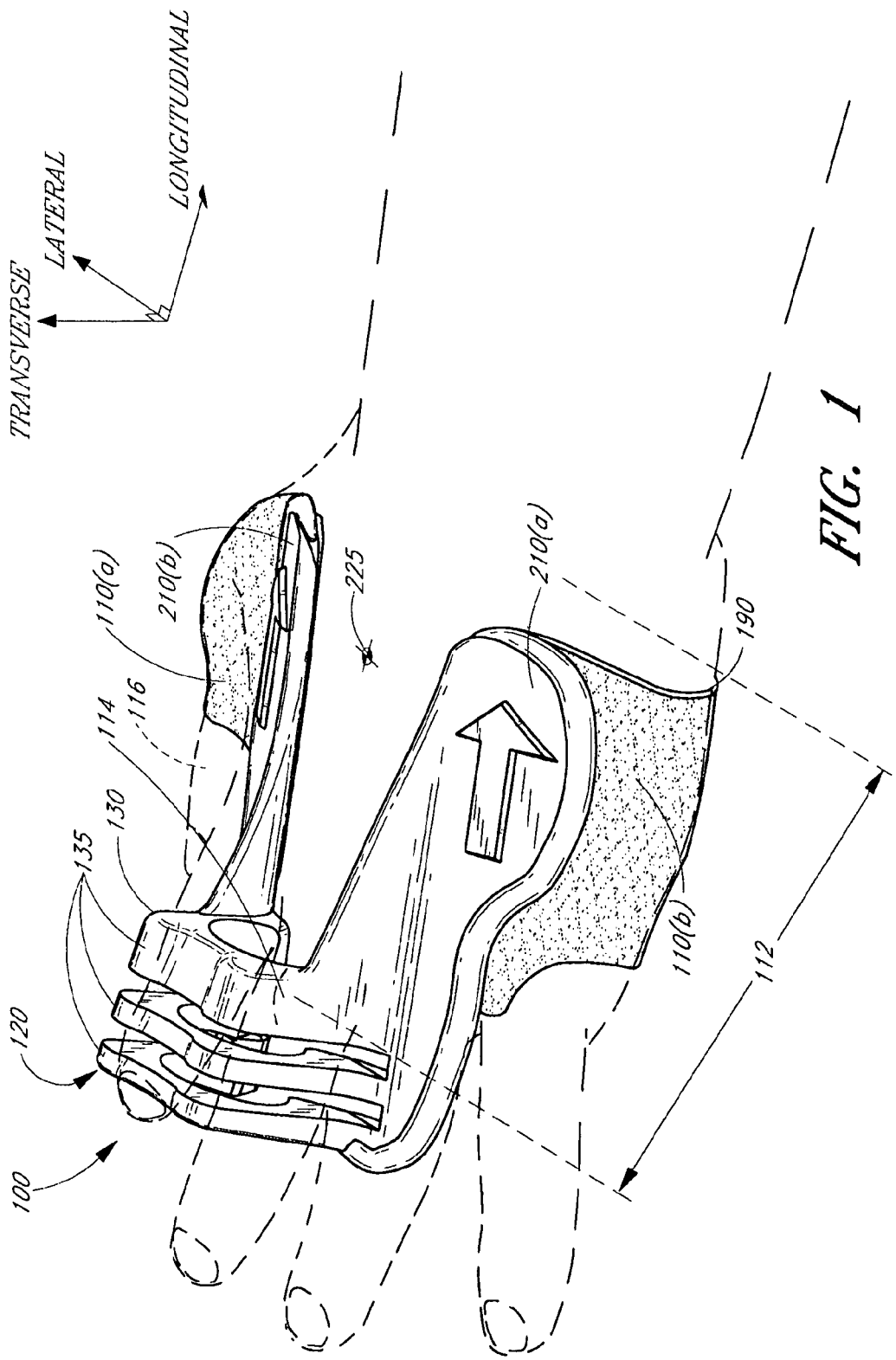
FIG. 1 is a perspective view of a securement device that is configured in accordance with a preferred embodiment of the present invention.

To assist in the description of these components of the securement system, the following coordinate terms are used (see FIG. 1). A "longitudinal axis" is generally parallel to a portion of the catheter hub or other medical article retained by the securement system, as well as parallel to the axis of a channel of the retainer, through which the medical article extends. A "lateral axis" is normal to the longitudinal axis. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The term "axial" as used herein refers to the axis of the channel or medical article, and therefore is substantially synonymous with the term "longitudinal" as used herein. Also, the terms "proximal" and "distal", which are used to describe the present securement system, are used consistently with the description of the exemplary applications (i.e., the illustrative examples of the use applications). Thus, proximal and distal are used in reference to the center of the patient's body. The terms "upper," "lower," "top," "bottom," "underside," "upperside" and the like, which also are used to describe the present securement system, are used in reference to the illustrated orientation of the embodiment. For example, the term "upperside" is used to describe the portion of the retainer that is located above a lateral axis that passes through the axis of the channel. The term "underside" is used to describe the portion of the retainer that is located below a lateral axis that passes through the axis of the channel. Brief introductions to some of the features, which are common to the described embodiments of the securement systems, are now described. In the illustrated embodiment, the arrows on the securement device point in the direction toward the insertion site (i.e., in the proximal direction).

Figure 2:
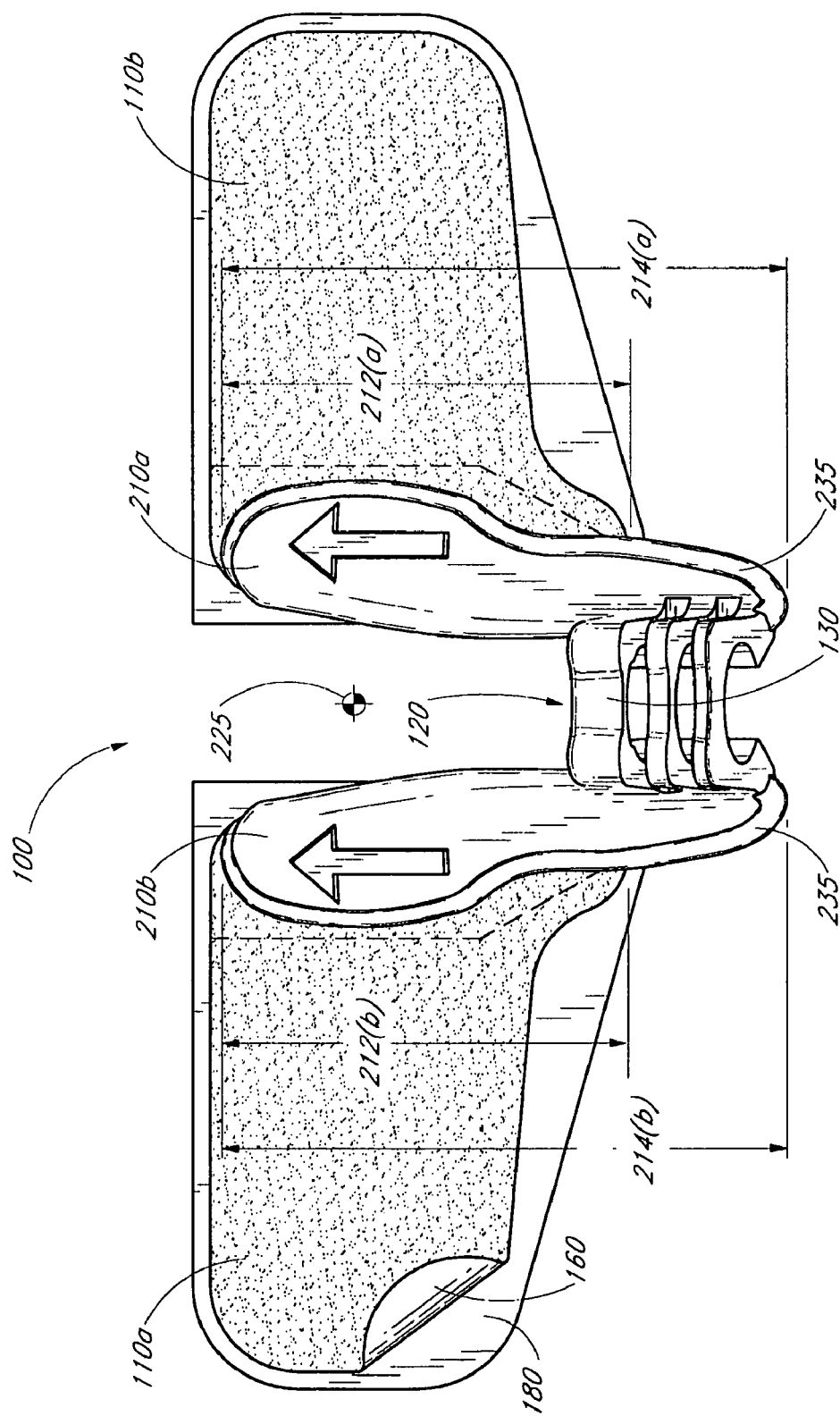
FIG. 2 is a top plan view of the securement device of FIG. 1 which includes a retainer and first and second anchor members.

Certain embodiments of the securement device have particular applicability in connection with securing a medical article to a neonate. The medical article may have an elongated body. The elongated body cooperates with the securement device to arrest movement of the medical article in longitudinal, lateral, and transverse directions. The securement device includes a body member and first and second mounting wings. An attachment portion (the longitudinal lengths of the attachment portions are illustrated in FIG. 2 as 212(a), 212(b)) of the bottom surface of each mounting wing attaches to an anchor member. The anchor members adhere to the skin of the neonate.

The attachment portions are disposed within the attachment region (see attachment region 112 in FIG. 1) when the securement device is secured to the neonate. Due to the difference in size between the medical article and the length of the attachment region on the neonate, the attachment portions of the mounting wings are offset in a proximal direction relative to the entire longitudinal length of the securement device.

The securement device permits the attachment portions of the retainer and the insertion site to both fit in the attachment region on the neonate. As illustrated by FIG. 1, at least a portion of the attachment region may be located on either side of the insertion site so as to inhibit movement of the medical article relative to the insertion site. The securement device can also be successfully utilized with any medical patient, notwithstanding the size or age of the patient. Thus, the illustration and description of the securement device in context of use a neonate is merely exemplary of one possible application of the securement device.

In each of the embodiments described below, the body member includes an inverted channel formed therethrough. The inverted channel has a longitudinal access opening located on an underside of the retainer to allow ingress and egress of the medical article. The medical article is installed or removed from the underside of the retainer via this access opening. Such an arrangement allows the medical provider to align at least a portion of the medical article with the retainer prior to fixing the retainer to the neonate's skin. In this way, the inverted channel retains a portion of the medical article.

The retainer includes at least one abutment (can be an abutment surface) that cooperates with at least one contact point or surface on the medical article. The one or more abutment extend generally normal to the axis of the channel and can be, for example, but without limitation, a surface, a wall of a slot, a ridge, a protuberance, or like structures. The abutment cooperates with the one or more contact points or surfaces of the medical article to inhibit longitudinal movement of the medical article through the channel. For example, the abutment could be a surface on the distal end of the retainer that acts against at least a portion of a radially extending member or spin nut of the medical article. In this way, the medical article will be limited in proximal movement (i.e., movement toward the patient) once the radially extending member contacts or abuts against the distal end of the retainer.

The mounting wings are disposed on the underside of the retainer at a position lower than the access opening and extend in a proximal direction away from the body member. The mounting wings provide an attachment surface for adhering the body member to the first and second anchor members. After the medical article is located in the retainer healthcare personnel attach the first and second anchor members to the neonate's skin. According to an aspect of the invention, the attachment portions of the mounting wings are disposed within the attachment region of the neonate.

Depending on the surface profile of the neonate's skin, a portion of the retainer may be elevated away from the neonate's skin and cantilevered relative to the attachments portions. For example, the attachment region may correspond to a dorsal portion of the neonate's hand (see FIG. 1) such that a distal portion of the retainer is suspended over the fingers. A soft or pliable material may be inserted between the distal portion and the neonate's skin to further inhibit rocking of the retainer relative to the attachment region on the neonate. In such an arrangement, a side view of a secured medical article would illustrate the attachment portions of the mounting wings (and the portions of the first and second anchor members transversely aligned with the attachment portions) offset in a proximal and longitudinal direction from the body member.

The retainer and first and second anchor members also can have other constructions in order to inhibit contact between the skin and the retainer, as well as between the skin and the retained portion of the medical article. For example, the anchor members can be thicker, in which case the lower surface of the mounting wings can be located higher on the body member and still maintain a gap between a secured medical article and the patient's skin.

To facilitate a complete understanding of the embodiment, the remainder of the detailed description describes the securement system with reference to the figures, wherein like elements among the embodiments are referenced with like numerals throughout the following description.

FIG. 1 is a perspective view of a securement device 100 configured in accordance with a preferred embodiment of the present invention. FIG. 2 is a top plan view of the securement device 100 of FIG. 1 showing a body member 130 at least partially offset along a longitudinal and distal direction from an attachment region 112 on the neonate. The attachment region 112 corresponds to the desired location for adhering the securement device to the neonate's skin. The attachment region 112 illustrated in FIG. 1 extends between the neonate's knuckle 114 and thumb 116. If the length of the attachment region 112 is sufficient to receive the entire retainer 120 and align the longitudinal axis of the medical article with the insertion site 225, the entire retainer 120 may be directly secured to the neonate's skin. If the attachment region 112 has a longitudinal length less than the overall length of the retainer 120, has a longitudinal curvature that prevents the entire retainer 120 from contacting the skin of the neonate, or if the desired location of the insertion site 225 prevents the entire retainer 120 from being adhered to the neonate's skin, a distal portion of the retainer 120 may be elevated from the skin of the neonate. In such instances, the healthcare provider can insert a soft material, for example, cotton or gauze, between the surface of the neonate and the elevated distal portion of the retainer 120 to thereby limit transverse motion or rocking of the retainer 120 upon the skin.

As shown in FIGS. 1 and 2, the illustrated securement device 100 comprises three main components: first and second anchor members 110(a), 110(b) and a retainer 120. The retainer 120 includes a first mounting wing 210(a) and a second mounting wing 210(b). The retainer 120 further includes a body member 130.

The first and second mounting wings 210(a), 210(b) are disposed below the body member 130 and extend in a proximal and longitudinal direction away from the body member 130 and generally towards an insertion site 225. As described below, a portion of each mounting wing 210(a), 210(b) is disposed upon the respective one of the anchor members 110(a), 110(b).

As illustrated in FIG. 2, the mounting wings 210(a), 210(b) are preferably disposed with respect to the body member 130 such that the tip of the medical article does not extend beyond the front or proximal edge of the mounting wings 210 when the medical article is properly inserted within the retainer 120. The healthcare provider can be instructed to generally align the medical article tip with the front edges of the anchor members 110(a), 110(b) before inserting the medical article into the retainer 120.

As most clearly shown in FIG. 2, the first mounting wing 210(a) has a longitudinal length 214(a). The second mounting wing 210(b) has a longitudinal length 214(b). The first mounting wing 210(a) and the second mounting wing 210(b) include attachment portions 212(a), 212(b), respectively. The attachment portions 212(a), 212(b) are spaced apart from each other in a lateral direction to define an insertion side space therebetween. In the embodiment illustrated in FIG. 2, the insertion side space is generally disposed at a position proximal of the body member 130. In the illustrated embodiment, the first and second mounting wings 210(a), 210(b) together support the body member 130 at a distal end of the insertion side space. A location along the mounting wing 210(a), 210(b) that is generally equidistant from the proximal and distal ends of the attachment portion 212(a), 212(b) defines a longitudinal midpoint of the attachment portion 212(a), 212(b).

Each attachment portion 212(a), 212(b) is disposed on a bottom surface of a mounting wing 210(a), 210(b). The attachment portions 212(a), 212(b) preferably align with at least a portion of the attachment region 112 on the neonate's skin. Such an arrangement enhances the stability of the securement device 100.

The attachment portion 212(a), 212(b) of each mounting wing corresponds with, and attaches to, a top surface of the corresponding anchor member 110(a), 110(b). Preferably, the longitudinal lengths of the attachment portions 212(a), 212(b) of the mounting wings 210(a), 210(b) are less than the corresponding longitudinal lengths 214(a), 214(b) of the mounting wings 210(a), 210(b).

FIG. 2 illustrates the attachment portion 212(b) as having a longitudinal length that is less than the longitudinal length 214(b) of the second mounting wing 210(b). Since the longitudinal length of the attachment portions 212(a), 212(b) is less than the longitudinal length of the corresponding mounting wing 210(a), 210(b), a distal portion of each mounting wing located below the body member 130 does not contact or adhere to the corresponding anchor member 110(a), 110(b).

FIG. 2 further illustrates the distal most ends of the attachment portions 212(a), 212(b) being located at the proximal side of the body member 130. Depending on, for example, the length of the attachment region 112 that is available for adhering the retainer 120 to the neonate, the distal ends of the attachment portions 212(a), 212(b) can be disposed so as to correspond to the proximal side of the body member 130 or, alternately, to correspond to another longitudinal point in between the distal and proximal ends of the mounting wings 210(a), 210(b).

Figure 19:
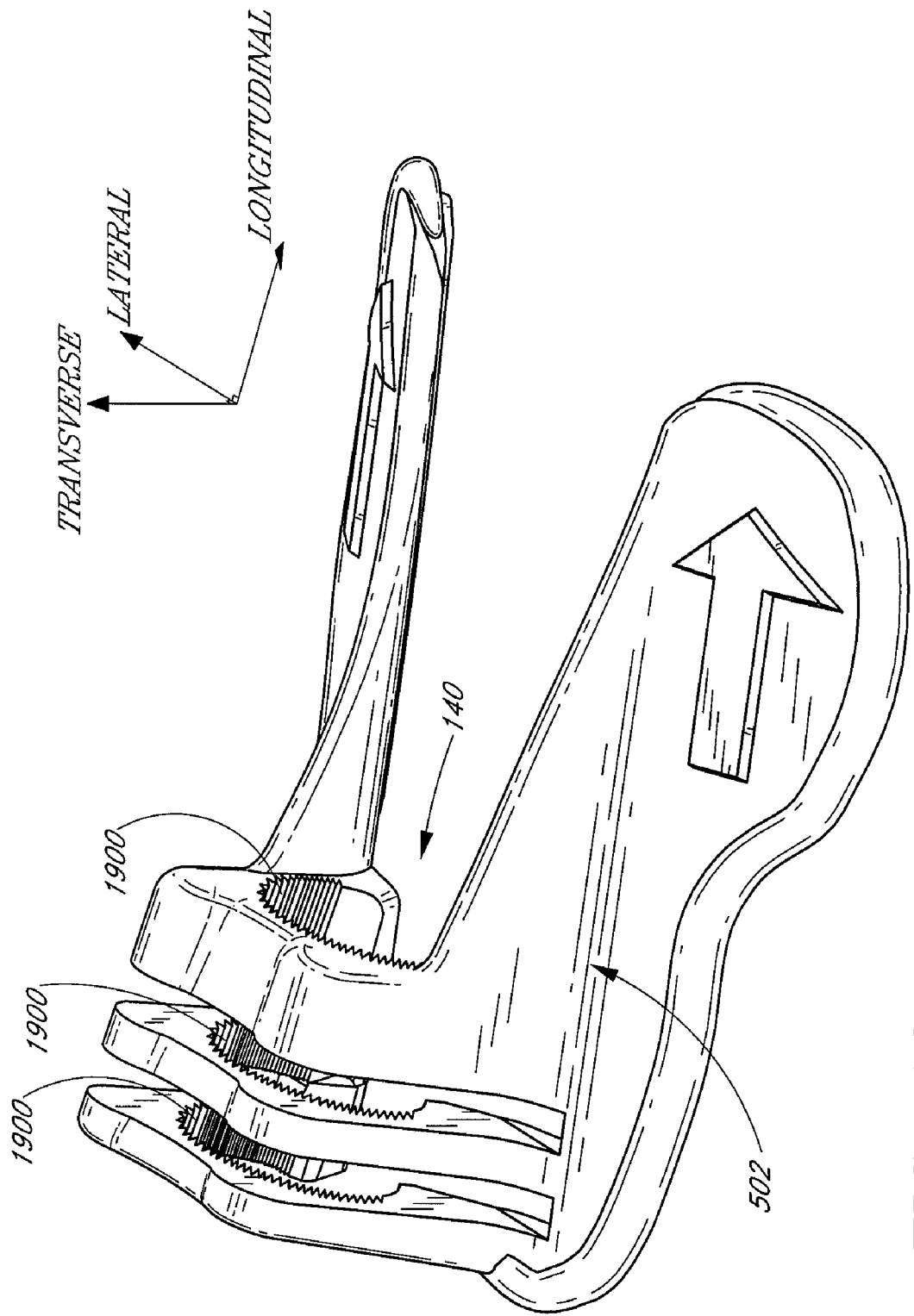
FIG. 19 is a perspective view of a securement device having splines distributed around the inside of the retainer for engaging and disengaging with a longitudinal extending member of the retained medical article.

Each mounting wing 210(a), 210(b) may include a support arm portion that links the attachment portion 212(a), 212(b) of the mounting wing 210(a), 210(b) to the portion of the mounting wing 210(a), 210(b) disposed below the body member 130 depending on where the distal end point of the attachment portion 212(a), 212(b) is disposed along the mounting wing 210(a), 210(b) relative to the proximal side of the body member 130. For example, the distal end point of the attachment portion 212(a), 212(b) may overlap with the body member 130, end at the proximal side of the body member 130, or be spaced from the proximal side of the body member 130 in the proximal direction. When spaced from the proximal side of the body member 130 in the proximal direction, the region of the mounting wing 210(a), 210(b) located between the distal end point of the attachment portion 212(a), 212(b) and the proximal side of the body member 130 defines the support arm portion of the mounting wing 210(a), 210(b). Accordingly, some embodiments of the mounting wing 210(a), 212(b) may not have a support arm portion. In the embodiment illustrated in FIG. 2 and as most clearly shown in FIG. 12, the distal end point of the attachment portion 212(a), 212(b) is disposed at the proximal side of the body member 130. An embodiment of a support arm 502 is shown in FIG. 19.

The longitudinal lengths of the attachment portion 212(a) and the attachment portion 212(b) are illustrated in FIG. 2 as being co-extensive. However, it may be advantageous for the length of the attachment portion for the second mounting wing 210(b) to be different than the length of the attachment portion for the first mounting wing 210(a). Such an arrangement may facilitate attaching the retainer 120 to an attachment region 112 on the neonate that is asymmetric across the longitudinal axis. Accordingly, one mounting wing 210 may include a support arm portion having a first longitudinal length while the other mounting wing 210 includes a support arm portion with a different longitudinal length or no support arm portion at all.

The lateral widths of the attachment portions 212(*a*), 212(*b*) may also vary between left and right mounting wings 210(*a*), 210(*b*). Such a construction may further enhance the securement device's applicability for use on uneven or asymmetric surfaces of the neonate's skin.

Figure 6:
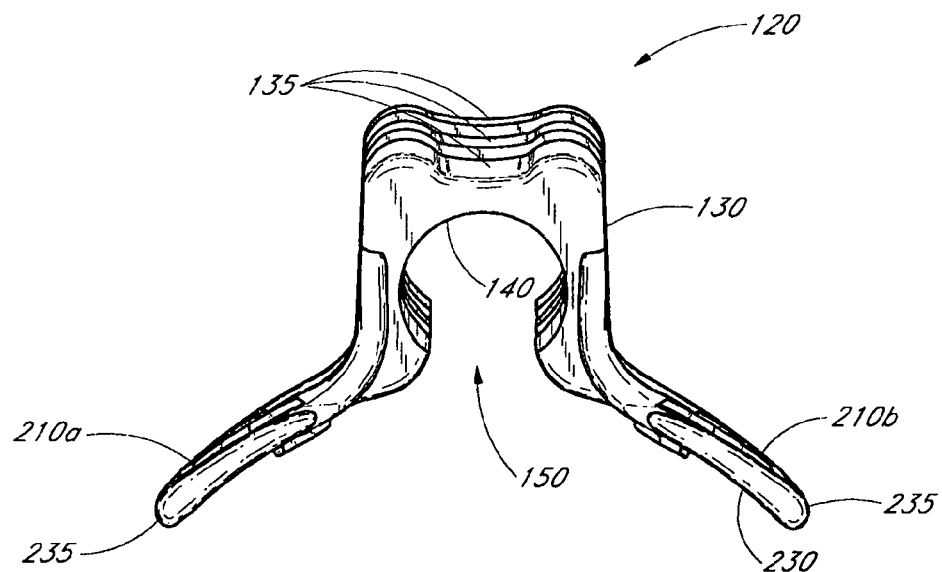
FIG. 6 is a front side view of the retainer of FIG. 5.

A perimeter edge or surface 235 around the mounting wings 210(*a*), 210(*b*) can be contoured to provide additional protection from chaffing or exfoliation caused by the perimeter edge bearing through the anchor member 110 and upon the neonate's skin. As best illustrated in FIGS. 1 and 6, the surface 235 around the perimeter of the mounting wings 210(*a*), 210(*b*) has a full radius with a diameter that exceeds a thickness of the mounting wing 210(*a*), 210(*b*). With the diameter exceeding the thickness of the mounting wings 210(*a*), 210(*b*), the added protection provided by the larger diameter does not substantially increase the weight of the securement device 100.

As noted above, the securement device 100 can form a component of a catheterization or securement system that also includes one or more medical articles, such as catheters, hubs, catheter adapters, fluid supply lines, or other articles suitable for securement via the anchor members and retainer. The catheterization system can also include a soft material, such as gauze, cotton, or other material suitable for insertion into any gap that is formed between the body member 130 and the neonate's skin. For example, inserting a cotton ball into a gap formed between the distal portion of the retainer 120 and the neonate's skin may provide additional rigidity to the retainer 120. Such a construction may be particularly advantageous when a portion of the body member 130 is cantilevered from the attachment region 112 and away from the neonate's skin.

Anchor Members

Figure 3:
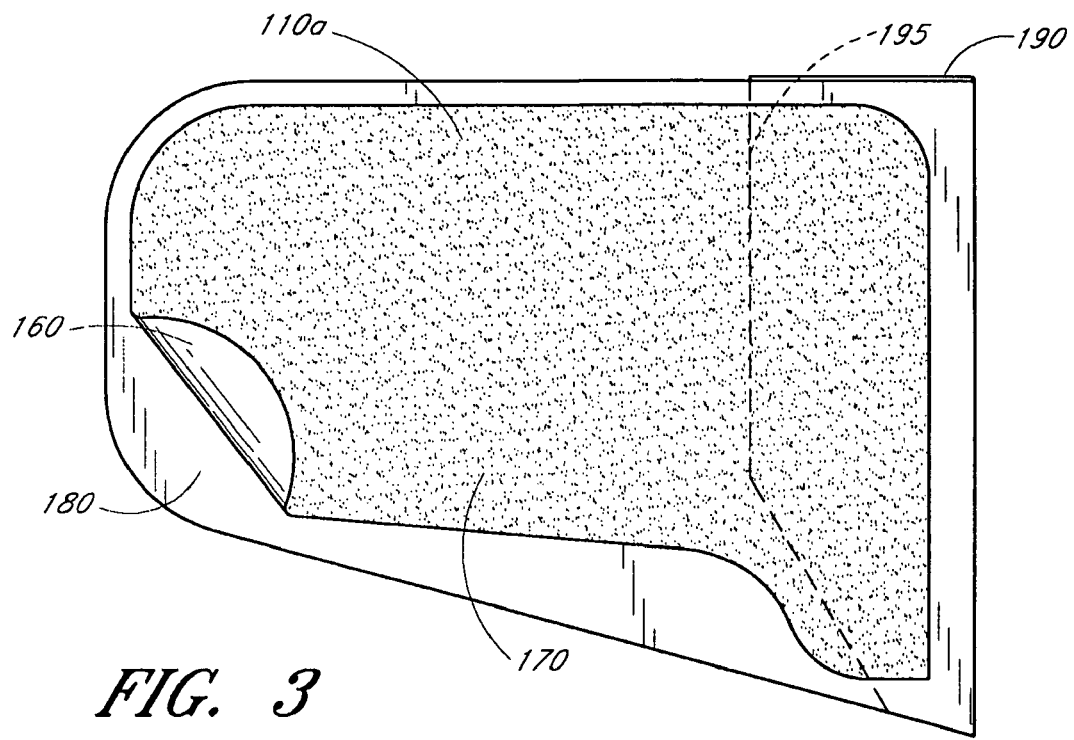
FIG. 3 is a top plan view of the first anchor member of FIG. 2.
Figure 4:
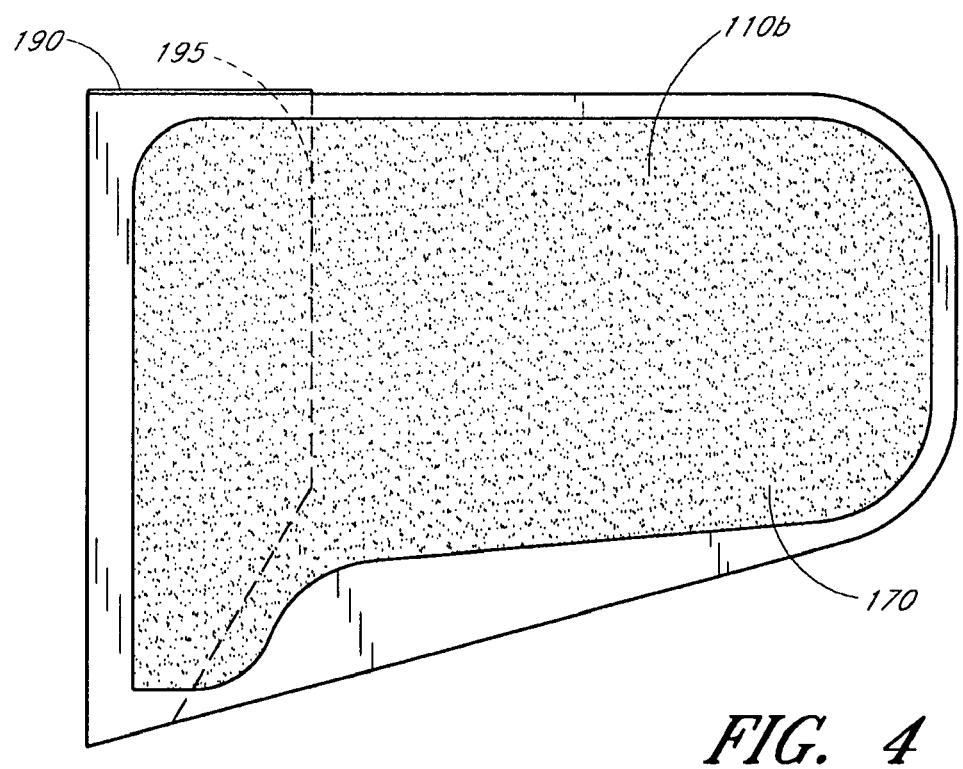
FIG. 4 is a top plan view of the second anchor member of FIG. 2.

FIGS. 3 and 4 illustrate the first anchor member 110(*a*) and the second anchor member 110(*b*), respectively, apart from the rest of the securement device 100 shown in FIG. 2. The general structure of each anchor member 110(*a*), 110(*b*) comprises a generally panhandle shape. In certain embodiments, the longitudinal extent of the anchor member 110 equals or exceeds the longitudinal extent of the attachment portion 212 of the corresponding mounting wing 210. Although only a single shape of the anchor member is illustrated in FIGS. 3 and 4, those of skill in the art will recognize that a variety of shapes can be used.

Each anchor member 110 comprises a laminate structure with an upper woven layer and a lower adhesive layer. The upper layer can be polyester or other suitable polymer or textile materials. One particular suitable material is woven polyester available commercially under the name "Tricot" from Tyco. In another variation, the upper layer is a plastic, paper or foam layer (for example, closed-cell polyethylene foam).

The lower adhesive layer constitutes a lower surface 160. The lower surface is a medical-grade adhesive and can be either diaphoretic or nondiaphoretic, depending upon the particular application. While not illustrated, the anchor members 110(*a*), 110(*b*) can include suture holes in addition to the adhesive layer to further secure the anchor member to the neonate's skin.

In other variations, a hydrocolloid adhesive or zinc oxide-based adhesive is used upon the anchor members 110(*a*), 110(*b*) for attachment to the skin of the neonate. The hydrocolloid or zinc oxide-based adhesive can be used either alone or in combination with another medical grade adhesive (for example, an adhesive available from Avery Dennison Corporation). Hydrocolloid and zinc oxide-based adhesives have less of a tendency to excoriate the skin of a patient when removed. This can be particularly important for neonates whose skin is more sensitive or fragile.

In variations where the upper layer has a foam surface, the upper surface 170 can be roughened by corona-treating the foam with a low electric charge. The roughened or porous upper surface can improve the quality of the adhesive joint (which is described below) between the mounting wings 210 and the anchor member 110.

As illustrated in FIG. 3, a removable paper or plastic release liner 180 covers the adhesive lower surface 160 before use. The liner 180 resists tearing and desirably is divided into a plurality of pieces to ease attachment of the tape to a patient's skin.

The liner 180 comprises a folded over portion to define a pull tab 190. The pull tab can be utilized to remove the paper or plastic release liner 180 from their adhesive lower surface 160 before use. A healthcare provider uses the pull tab 190 by grasping and pulling on it so that the liner 180 is separated from the lower surface 160. The pull tab 190 overcomes any requirement that the healthcare provider pick at a corner edge or other segment of the liner in order to separate the liner from the adhesive layer.

In the embodiment illustrated in FIGS. 3 and 4, the pull tab 190 extends from a bottom surface of the anchor member 110(*a*), 110(*b*) and along an inner line 195. The pull tab 190 of course can be designed in a variety of configurations. For example, the pull tab 190 can be located along a center line of the anchor member 110; or alternatively, the pull tab can be located along any line of the anchor member 110 in order to ease the application of the anchor member onto the neonate's skin at a specific site. For example, an area of a neonate's skin with an abrupt bend, such as at a finger joint, can require that the pull tab 190 be aligned toward one of the lateral ends of the anchor member 110.

The projection of the release liner beyond the anchor member inner edge provides an area onto which any adhesive, which is used to attach the retainer to the anchor member, can run while lessening the occurrence of such adhesive contacting the fold. Cracks often occur at the fold and presence of adhesive in such cracks can create delimitation of the release liner and incomplete removal of the release liner when peeled away from the corresponding anchor member 110(*a*), 110(*b*).

Retainer

Figure 5:
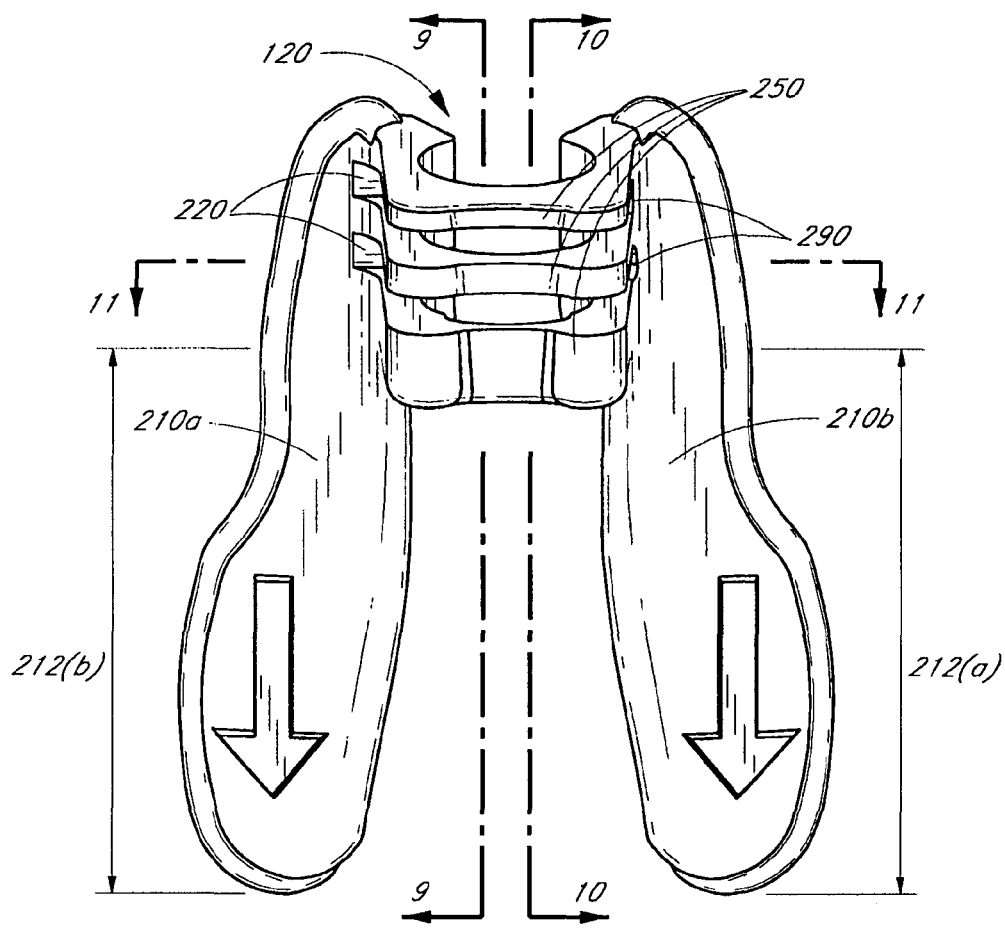
FIG. 5 is a top plan view of the retainer of FIG. 2.

The retainer 120 is further described with reference to FIGS. 5 through 13. FIG. 5 is a top plan view of the retainer 120 of FIG. 2 and further illustrates the body member 130 as well as the first and second mounting wings 210(*a*), 210(*b*). As illustrated in FIG. 5, the first and second mounting wings 210(*a*), 210(*b*) extend from a proximal most side of the body member 130.

Figure 7:
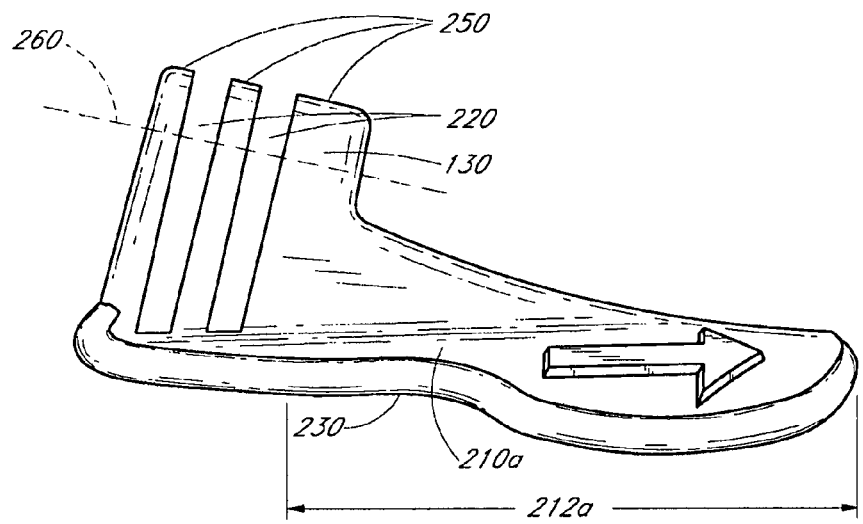
FIG. 7 is a side view of the retainer of FIG. 5.
Figure 8:
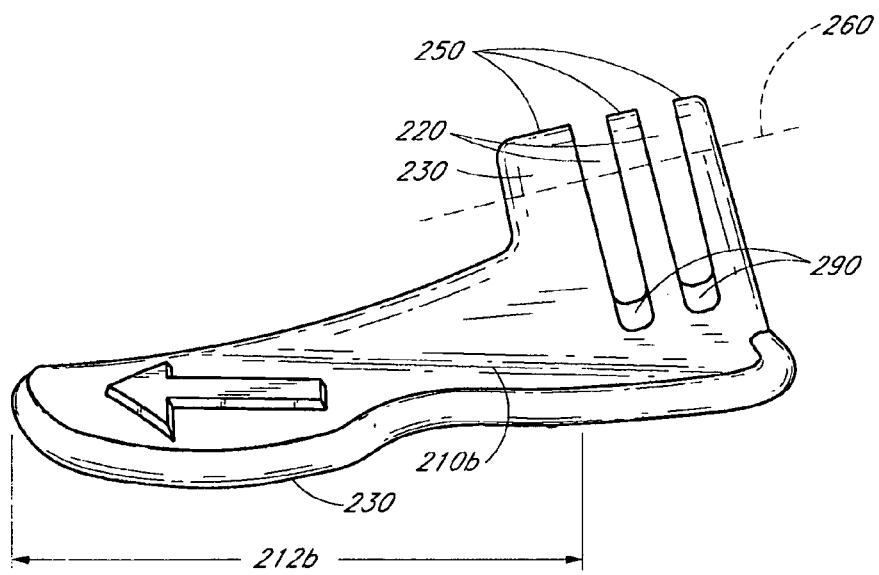
FIG. 8 is a side view of the retainer of FIG. 5.

FIG. 6 is a front side view of the retainer 120. As shown in FIGS. 7 and 8, the body member 130 portion of the retainer 120 and the attachment portions 212(*a*), 212(*b*) of the mounting wings 210(*a*), 210(*b*) are at least partially offset from each other along the longitudinal axis.

The body member 130 is elongated in the longitudinal direction and comprises a generally parallelepiped shape. It is advantageous for the longitudinal dimension of the body member 130 to be sufficiently long to enhance the stability of the retained portion of the medical article along its length. The lateral width of the body member 130 is selected so as to allow the healthcare provider to easily and naturally grip the securement device 100.

With reference to FIG. 6, the inner side of the body member 130 faces towards the patient's skin when in use and defines an inverted central channel 140. The inverted channel 140 extends on the underside of the body member 130 in a longitudinal direction for receiving a section of the medical article. A location along the longitudinal direction that is generally equidistant from the proximal and distal ends of the body member 130 defines a longitudinal midpoint of the channel 140.

The channel 140 is capable of receiving a portion or length of the medical article and is generally configured to house, to grip, and to secure this portion of the medical article. In the illustrated embodiment (see FIGS. 5 through 8), the central channel 140 has a generally semi-circular cross-sectional shape. An inner surface contour of the central channel 140 suitably is selected depending on the geometry of the portion of the medical article to be retained. For example, in a retainer 120 that is configured to retain a portion of a medical article that has a constant outer diameter, the central channel 140 suitably has a constant radius along its length. In contrast, in a retainer 120 configured to retain a portion of a medical article that has a tapering outer surface, the central channel 140 suitably has a tapering inner surface and a radius that varies along the channel length.

Additional embodiments of the central channel 140 of the retainer can comprise a plurality of different radii and/or tapering regions. For example, the channel 140 can have two sections: a first proximal section have a generally uniform cross-sectional size along its length while a second distal section has a tapering shape along its length. An abutment wall may form a transition between these two sections of the channel. These sections of the channel 140 can also both be tapered or straight (i.e., have a generally uniform radius along the length of the section) or the distal section can be straight and the proximal section can be tapered. In this way, the size and shape of the central channel 140 can be chosen to match or to approximate the size and shape of the medical article or portion thereof, e.g., the catheter hub, to be retained.

By matching the inner surface contour of the central channel 140 to the outer surface of the secured portion of the medical article, a more effective securement may be achieved. In addition or in the alternative, effective securement can also be achieved by the engagement of one or more abutment surfaces of the retainer with one or more contact surfaces on the medical article. Each abutment surface can cooperate with a contact surface on the medical article to inhibit movement of the medical article relative to the retainer. Exemplary abutment surfaces and contact surfaces are described below with reference to FIGS. 16-18.

Although the central channel 140 can be formed in various shapes depending upon the desired application (e.g., depending upon a shape of the retained portion of the medical article for which the retainer is designed to be used), the central channel 140 desirably has a sufficient length in the longitudinal direction to stabilize the catheter hub, or other medical article, rather than act as a fulcrum for the fitting. That is, the retainer 120 receives a sufficient length of the catheter hub to inhibit movement of the hub in the lateral, longitudinal and transverse direction (i.e., to inhibit yaw, pitch and axial movement of the article).

Figure 12:
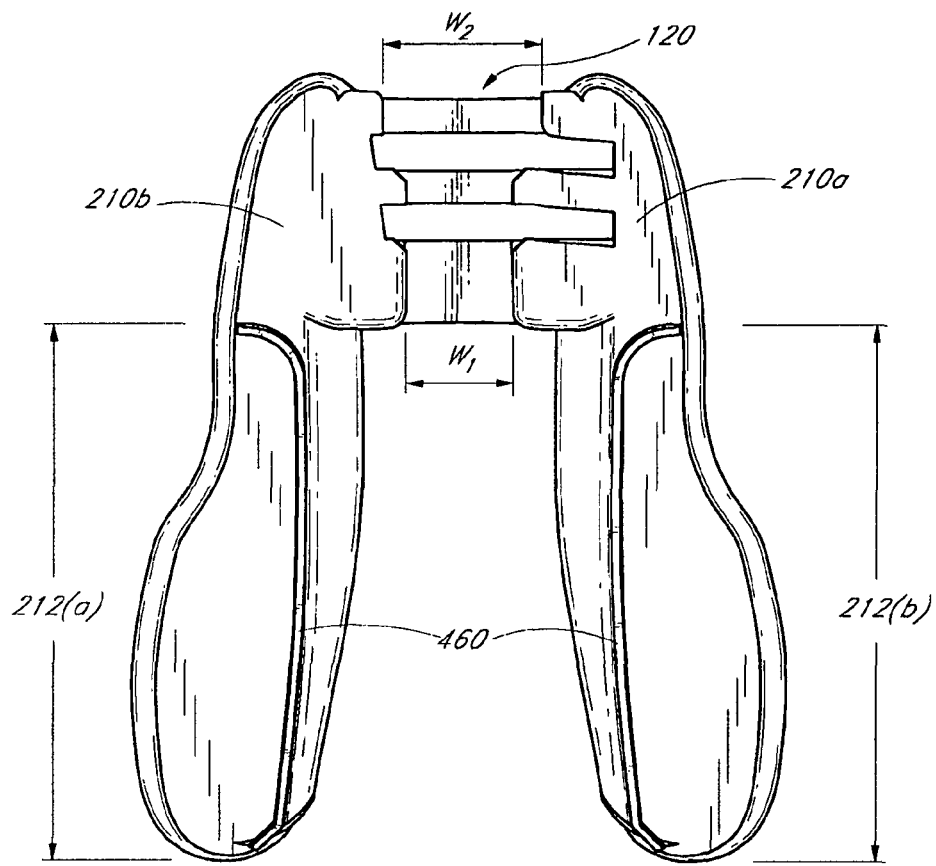
FIG. 12 is a bottom plan view of the retainer of FIG. 5 and illustrates that the distance between the side mounting wings varies in the region of the retainer.

As shown most clearly in FIGS. 6 and 12, the lower side of the retainer 120 includes an access or lower opening 150. In the illustrated embodiment, the lower opening 150 has generally tapering sides along the longitudinal axis to match generally the shape of the medical article. In other embodiments, the lower opening 150 has generally parallel sides while the channel 140 is tapered to match generally the shape of the medical article. The lower opening 150 may include contouring (e.g., chamfers) along its periphery in order to guide the medical article into the central channel 140 when inserting the medical article into the retainer 120.

The illustrated retainer 120 further comprises at least one retention surface 165(a), 165(b) disposed on a lower side of the inverted channel 140. The at least one retention surface 165 supports the medical article so that the medical article is elevated in the retainer 120 such that the retained portion of the medical article (e.g., the retained portion of the catheter hub) is raised from the neonate's skin to lessen or eliminate compression, excoriation, and/or chaffing of the skin. Thus, the retainer 120 lifts and holds the retained portion of the catheter hub up from the patient's skin.

This support can be provided by, for example, an adhesive, a region of the inverted channel which provides a degree of snap-fit with the retained medical article, two or more regions of the inverted channel which provide a degree of snap-fit with the retained medical article, or a combination of the adhesive and a region of snap-fit. The adhesive can be located on one or more surfaces of the retainer 120 that contact the medical article. For example, the adhesive could be located on the surface of the inverted channel or on an abutment.

Figure 9:
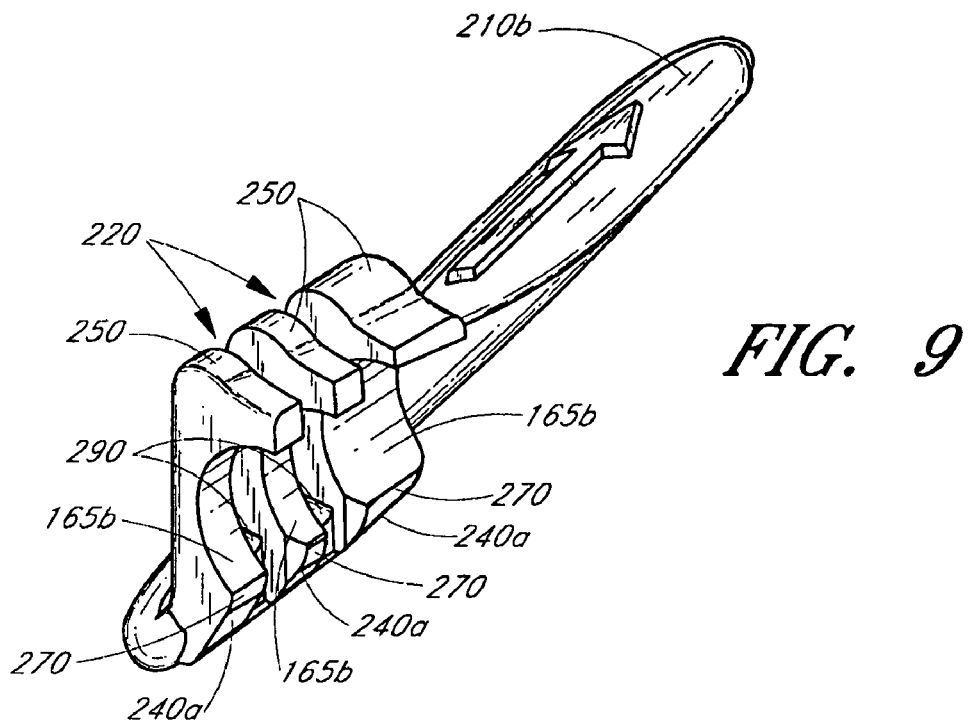
FIG. 9 is a cross-section view of the retainer taken along section 9-9 of FIG. 5.
Figure 10:
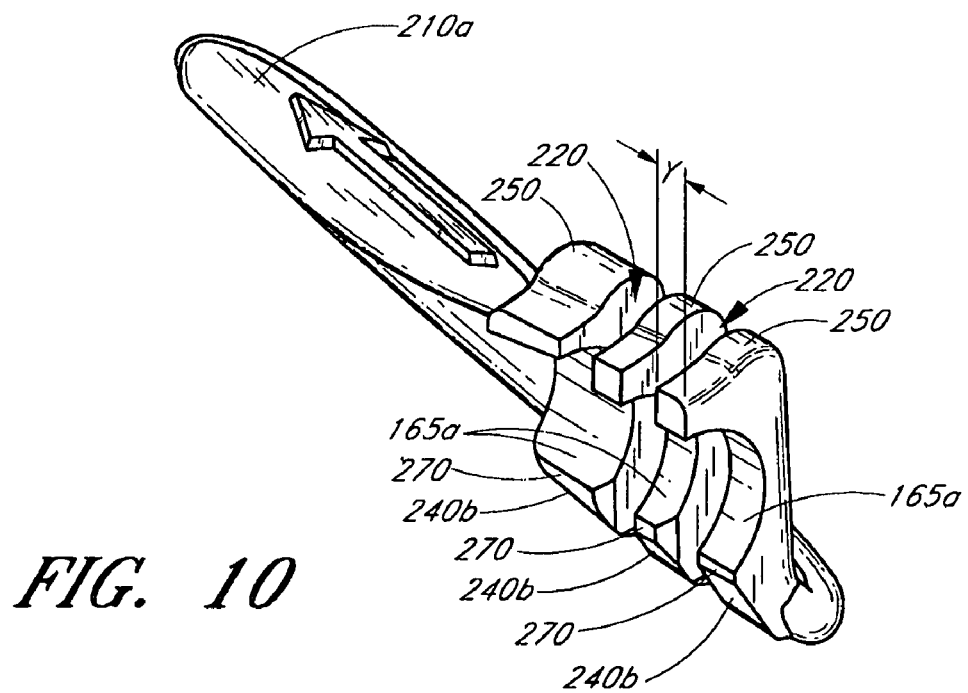
FIG. 10 is a cross-section view of the retainer taken along section 10-10 of FIG. 5.
Figure 11:
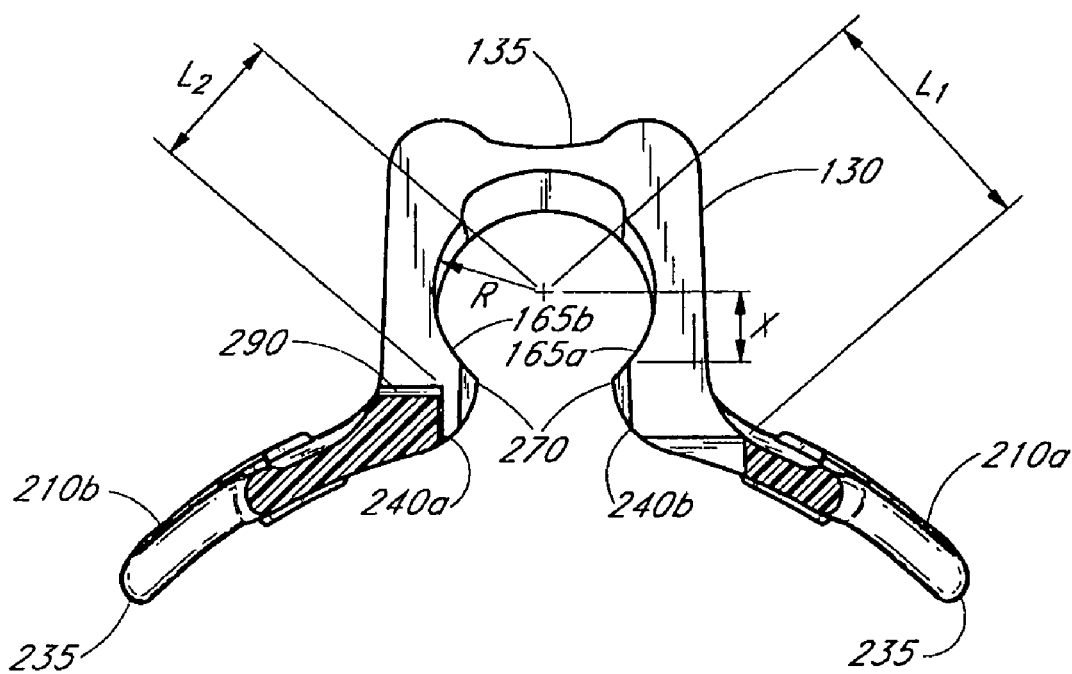
FIG. 11 is a cross-section view of the retainer taken along section 11-11 of FIG. 5 and illustrates an optional wall or stop member that extends into the path of the one or more slots in the region of the mounting wing.

As shown most clearly in FIGS. 9 through 11, the present embodiment of the retainer 120 includes multiple pairs of retention surfaces 165(a), 165(b). The corresponding retention surfaces 165(a), 165(b) of each pair lie on opposite sides of the access opening 150 from each other. In this embodiment, the retention surface 165(a) is a portion of the surface that defines the central channel 140 and is located on the lower side of the central channel 140. The retention surface 165(a) is located to one side of the central axis. The other retention surface 165(b) is a portion of the surface that defines the central channel 140 and is located on the lower side of the central channel 140. The retention surface 165(b) is further located to the side of the central axis that is opposite to the retention surface 165(a). Once the medical article is placed in the central channel 140, the retention surfaces 165(a), 165(b) each hold a portion of the retained section of the article within the channel 140. While multiple retention surfaces are illustrated in FIGS. 9 through 11, either retention surface 165(a), 165(b) can be individually employed in variations of the present retainer and still support the medical article within the channel 140.

As shown most clearly in FIG. 11, the retention surfaces 165(a), 165(b) are both located generally at a distance X measured in a transverse direction from the axis of the central channel 140. Distance X is less than radius R when measured at the same location along the central channel 140 to elevate the retained medical article above the neonate's skin.

The retention surfaces 165 provide a degree of snap fit between the retainer 120 and the medical article. The degree of snap-fit can be increased by extending the overall surface of the central channel 140 through an arc of greater than 180°. As shown most clearly in FIG. 6, the arc extends for more than 180 degrees in order to more firmly support the retained portion of the medical article. In the illustrated embodiment, the walls of the central channel 140 extend through an arc of approximately 270°. The length of such an arc provides a snap-fit securement between the central channel 140 on the body member 130 and the secured portion of the medical article. In this way, the medical article can be placed in position prior to attaching the securement device 100 to the patient without concern that the medical article will shift while healthcare personnel is attaching the device 100 to the patient. Additionally, the releasable engagement provided by snap-fit connection also permits the retained portion of the medical article to be readily released from retainer 120.

In the illustrated embodiment, as best seen in FIG. 11, chamfered surfaces 240(a) are formed on the underside of the body member 130 along one of the lower edges of the access opening 150. A second set of chamfered surfaces 240(b) is formed on the underside of the body member 130 along the other lower edge of the access opening 150. The portions of the body member 130 between these chamfered surfaces 240 and the retention surfaces 165 form hips 270. In other words, the hips 270 are the portion of the body member 130 that is defined by a lower side of the central channel 140 (either the retention surfaces 165(a) on one side of the central axis or the retention surfaces 165(b) on the other side of the central axis), the chamfered surfaces 240, and the sides of the narrow lower opening 150. In one embodiment, the chamfered surfaces 240(a) on one side of the central axis are disposed at an oblique angle to the chamber surfaces 240(b) on the other side of the central axis and help guide the medical article into the lower opening 150 and the central channel 140.

The retainer 120 can include a generally rigid structure (at least in comparison to foam or tape) and is principally defined by the body member 130 and the first and second mounting wings 210(a), 210(b). The body member 130, however, may be somewhat flexible in nature, due both in part to its structure and to the material used to form the body member 130. Suitably rigid but flexible materials include, for example, but without limitation: plastics, polymers or composites such as polypropylene, polyethylene, polycarbonate, polyvinylchloride, acrylonitrile butadiene styrene, nylon, olefin, acrylic, polyester, as well as moldable silicon, thermoplastic urethane, thermoplastic elastomers, thermoset plastics and the like. However, other materials can be utilized.

The body member 130 and mounting wings 210(a), 210(b) are integrally formed to comprise a unitary retainer. This can be accomplished in any of a variety of ways well known to those skilled in the art. For instance, the entire retainer 120 can be injection molded in order to reduce fabrication costs. The illustrated retainer 120 is formed by injection molding using polyethylene or polypropylene material. The retainer 120, however, can comprise a non-unitary body member 130 and mounting wings 210(a), 210(b). In this manner, the body member 130 and one or both of the mounting wings 210(a), 210(b) is formed separately and then coupled together. Additionally, the body member 130 and mounting wings 210(a), 210(b) can have other forms and can have other orientations relative to one another. The body member 130 also can be clear or transparent to facilitate alignment of the retainer 120 with the catheter hub or other medical article during insertion of the medical article through the access opening 150.

As illustrated in FIG. 12, each mounting wing 210(a), 210(b) comprises a glue dam 460 around a portion of its periphery on its underside. The glue dam restricts adhesive flow beyond an inner edge of the respective mounting wing. The outer edge of each mounting wing 210(a), 210(b) does not include the glue dam (as best seen in FIGS. 11 and 12) to allow any excess glue or adhesive to seep out from under the mounting wing during the manufacturing process in the lateral direction away from an axis through the retainer 120.

As is shown in FIG. 2, the body member 130 is attached to the mounting wings 210(a), 210(b) in a region that is distal of the attachment portions 212(a), 212(b), however, it need not be so. The attachment portions 212(a), 212(b) may, or may not, overlap with the body member 130.

At least a part of the attachment portion 212(a) of the mounting wing 210(a) suitably aligns with the attachment region 112 of the skin of the neonate. Similarly, at least a part of the attachment portion 212(b) suitably aligns with the attachment region 112. The body member 130 and mounting wings are desirably secured to the upper surface of the first and second anchor members 110(a), 110(b) by a solvent bond adhesive, such as cyanoacrylate or other bonding material. One such adhesive is available commercially as Part No. 4693 from 3M.

When the anchor members 110 are secured to the skin of the neonate, the medical article is inhibited from moving substantially in either the lateral or transverse directions relative to the neonate. Longitudinal movement of the medical article is inhibited by engagement between at least one abutment surface on the retainer 120 and a contact surface or mating surface on the medical article. The abutment surface on the retainer 120 extends generally normal to the axis of the central channel 140. The abutment surface can be located at or between the distal and proximal ends of the retainer 120. For example, the abutment surface can be either the proximal or distal ends of the retainer. Moreover, multiple abutment surfaces on the retainer 120 can be employed with each abutment surface being the same or a different type of abutment surface. Additionally, the abutment surface can be used to arrest movement in one longitudinal direction and the shape of the channel can be used to arrest movement in the opposite longitudinal direction. For example, at least a portion of the channel 140 can have a tapering inner surface and the retainer can include an abutment surface in the form of the proximal end of the retainer. The tapering shape and abutment surface cooperate to inhibit longitudinal motion in both longitudinal directions. In such an embodiment, the tapering surface contacts an outer tapering surface of the medical article to limit motion in one direction. Likewise, the proximal end of the retainer abuts with a radially extending member on the medical article to limit motion in the opposite direction.

The retainer 120 thus includes one or more abutment surfaces. In the illustrated embodiment, the retainer includes multiple abutment surfaces that are formed by one or more slots 220 in the body member 130. In the form of a slot 220, one abutment surface forms one side of the slot and another abutment surface forms the other side of the slot 220.

To arrest longitudinal motion in the illustrated embodiment, two contact surfaces in the form of a single radially extending member are employed on the medical article. The radially extending member extends through the slot 220 in the retainer 120 to inhibit longitudinal motion of the medical article in both longitudinal directions. The contact between the two abutment surfaces on the retainer 120 and their corresponding contact surfaces on the medical article arrests motion in the longitudinal direction. Further embodiments of the retainer 120 inhibit rotational movement of the installed medical article. This will be discussed in greater detail below.

As shown in FIG. 5, the retainer 120 includes pairs of abutment surfaces with each pair forming one lateral slot 220 (preferably four abutment surfaces form at least two slots) that are sized to receive a radially extending portion of the catheter (e.g., a push tab 310 that extends from a catheter hub 430). These slots 220 can extend circumferentially about at least a portion of the axis of the central channel 140. Each slot has a longitudinal length sufficient to accept the radially extending member of the retained medical article.

The radially extending portion of the medical article is in the form of a push tab 310. An embodiment of a push tab 310 is described with reference to FIGS. 14 and 15. In particular, it can be desirable for the longitudinal length of each slot to be sufficient to receive the push tab 310 of the medical article; however, each slot 220 can be slightly larger than the push tab's thickness (as measured in the longitudinal direction)

and a gap can exist between one or both sides of the push tab 310 and the corresponding abutment surfaces that define the slot 220 into which the push tab 310 has been inserted. In a preferred form, at least two or three annular slots 220 are disposed within the retainer 120. The longitudinal length of each slot 220 can be about five thousandths of an inch (0.005 inch, 0.127 mm) larger than the radially extending member (e.g., the push tab 310). Such an arrangement can be desirable to minimize longitudinal movement of the retained portion (e.g., the tab 310 in FIG. 15) of the medical article. Accordingly, a small gap can exist between any abutment surface and a corresponding contact surface before the medical article is shifted relative to the retainer 120. Once shifted, however, further longitudinal movement is prevented by the interference between the contact surface and the abutment surface.

Those of skill in the art will recognize that each slot 220 need not have identical radial extent. The radial extent of each slot 220 need not be uniform about the axis of the central channel 140.

The inner edges of each slot 220 can be chamfered so as to ease the insertion of a radially extending member into any slot 220. By having the edges of each slot chamfered, it becomes possible to move a radially extending member 310 into a slot 220 even if the initial alignment between the center of the slot and the center of the radially extending member is not exact. The use of chamfered edges on the slots 220, as well as the presence of slots located at multiple longitudinal positions along the length of the central channel 140, allows for a medical article to be placed into the central channel of the retainer 120 with only coarse alignment with the axis of the central channel. The medical article generally moves into the nearest slot 220 as the medical article is pressed up into the retainer 120 from below (that is, as the retainer 120 is pressed over the retained portion of the medical article). The chamfered surfaces 240(a), 240(b) adjacent to the mounting wings 210(a), 210(b) help guide the medical article into the central channel 140. The alignment process is further facilitated when a portion of the retainer 120 is transparent.

Figure 13:
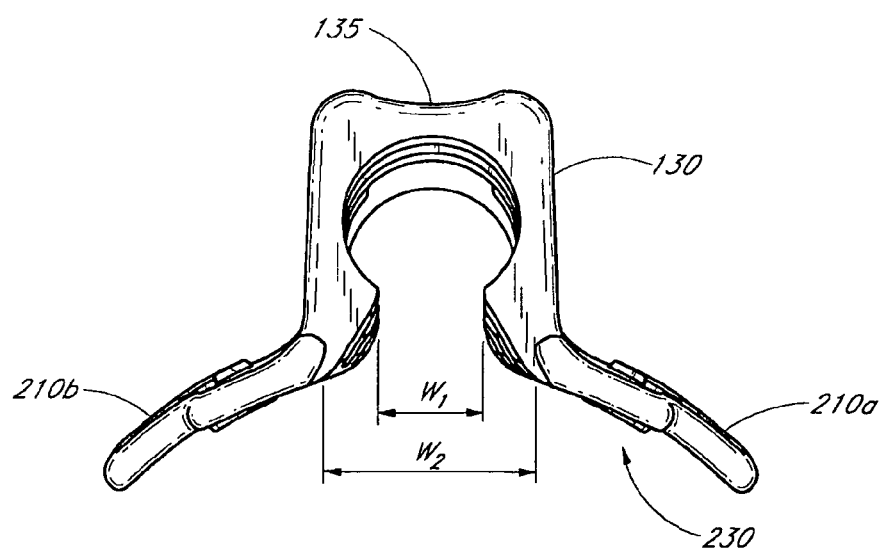
FIG. 13 is a rear side view of the retainer of FIG. 5.

As shown most clearly in FIGS. 6, 11, and 13, an upper section of the retainer 120 further comprises a depression 135 which forms a finger pad that a healthcare provider can press down upon. The depression 135 encourages the finger to push down on the retainer 120 and discourages the healthcare provider from gripping the retainer 120 on its sides during application. Such a side grip could squeeze or constrict the retainer 120 and make it harder to slip the retainer 120 over the medical article. By pushing down on the retainer 120, this constrictive effect is avoided.

As illustrated in FIGS. 6 and 13, a base surface 230 of the retainer 120 can have a concave curved shape when viewed from the front and rear sides. The degree of curvature can be varied depending on the expected location of usage or application of the securement device 100. It will be appreciated that many common sites for insertion of medical lines which require securement will be located on anatomical regions exhibiting convex curvature, such as a dorsal side of a neonate's hand, a arm, a leg, a contact surface, etc. By providing a concave bottom profile to the retainer 120, the retainer will rock less once placed upon the neonate via the first and second anchor members 110(a), 110(b).

FIGS. 7 and 8 are side views of the retainer 120 of FIG. 5. As illustrated in FIGS. 7 and 8, an axis 260 of the central channel 140 lies at an angle with respect to the base surfaces 230 of the retainer 120. The desired angle between the medical article and the patient is created by angling the axis 260 of the central channel 140. This angle is selected in order to align the axis 260 of the channel 140 of the retainer with the desired incident angle with which the medical article is to contact the skin of the neonate.

A variety of different angles for the central channel 140 can be used, ranging from 0° to 45°, and more preferably from 5° to 25°. For instance, for the securement of intravenous catheters, it is desirable for the angle of incidence of the catheter to the skin of the neonate to be between about 7° to about 15°. For the securement of arterial catheters, it is desirable for the angle of incident of the catheter to the skin of the neonate to be about 12.5°. By angling the axis 260 of the channel 140 at the desired angle, which will depend upon the particular securement application (e.g., securing an arterial catheter, an intravenous catheter, etc.), the proper angle of incidence for a catheter can be maintained.

While not illustrated, the retainer 120 can further comprise ribs. The ribs project away from the outside surface of the channel 140. Such ribs may be formed by extending portions of the slots 220 of the retainer 120 away from the channel 140. The ribs provide additional surfaces for the healthcare provider to grip the retainer 120.

As shown most clearly in FIGS. 5 and 7 through 10, located adjacent to the slots 220 are upper sections 250. The thickness of the upper sections 250 in the longitudinal direction can vary in order to maintain a generally constant spring force along the entire length of the retainer 120. In this way, the same amount of force is required to spread the walls of the retainer 120 apart even though in the illustrated embodiment the back end of the retainer 120 spreads more to receive the larger diameter section of a tapered catheter hub 430. As illustrated in the cross-section views of FIGS. 9 and 10, the longitudinal and transverse lengths of the upper sections 250 vary between one or more of the upper sections.

Although certain features of the retainer 120 can be specifically configured for use with a catheter hub 430, it will be understood by those of skill in the art that such a retainer 120 can be used with other adaptors or medical lines as well.

As shown in FIGS. 5 through 13, each slot 220 is substantially annular in form. However, as illustrated most clearly in FIG. 11, a stop member or wall 290 extends into the path of the one or more slots 220 at a circumferential location about the axis of the central channel 140. A comparison of FIGS. 9 and 10 illustrates that the wall 290 in the illustrated embodiment is located on the second mounting wing 210(b) side of the retainer 120. As shown in FIG. 11, the wall 290 in the illustrated embodiment extends in a lateral direction away from the second mounting wing 210(b) and into one or more slots 220. In this way, the wall 290 limits the rotation of the radially extending member and medical article when the medical article is installed in the retainer 120. Thus, in the illustrated embodiment, one or more slots 220 extend circumferentially about the axis of the central channel 140 for less than 360 degrees.

The wall 290 can be located at other locations around the circumference of the central channel 140. For example, the wall 290 could extend in a lateral direction away from the first mounting wing 210(a) and into one or more slots 220. In embodiments of the retainer 120 where the wall 290 extends into less than all of the slots 220, the healthcare provider can select whether to restrict the rotation of the medical article. For example, the healthcare provider can restrict the rotation of the medical article by inserting a radially extending member of the medical article into a slot 220 that includes the wall 290. Alternatively, the healthcare provider can install the radially extending member into a slot 220 that does not include the wall 290 to allow unbridled rotation of the medical article. Moreover, more than one wall 290 can be located around the circumference of the one or more slots 220 to further limit the rotation of the medical article. In still further variations of the retainer, the retainer can omit the wall(s) 290.

Each slot 220 has a lateral width sufficient to receive the radially extending member of the medical article. In this way, the retainer 120 is designed to grip non-winged catheters regardless of the position of the radially extending member. For example, in the illustrated embodiment, a catheter hub 430 can be installed into the retainer 120 regardless of rotation of the catheter hub 430 about its axis except when the catheter hub 430 is rotated such that the radially extending member coincides with the wall 290. The slot 220 can initially receive the radially extending member whether the radially extending member is pointing away from the patient, toward the patient, to either side, or generally at any other angle about the axis of the catheter hub 430. However, when the radially extending member is pointing directly to the left side and the catheter hub 430 enters the access opening 150, the radially extending member contacts the wall 290. As the catheter hub 430 is further installed into the retainer 120, the catheter hub 430 is forced to rotate such that the radially extending member is pointing downward. When the radially extending member is pointing downward, the radially extending member will follow the catheter hub 430 into the retainer 120 as the catheter hub 430 is inserted through the access opening 150. Once the catheter hub 430 has rotated and is subsequently fully installed in the retainer 120, the wall 290 will not allow the catheter hub 430 and radially extending member to rotate completely about the axis of the central channel 140. For example, as the catheter adapter is rotated, the radially extending member of the catheter hub 430 slides within the slot 220. However, at some point during the rotation of the catheter hub 430, the radially extending member contacts the wall 290.

In the embodiment illustrated in FIGS. 5 through 13, the wall 290 limits the rotation of the radially extending member when the push tap is sufficiently rotated in either direction towards the second mounting wing 210(*b*) side of the retainer 120. In this way, the wall 290 prohibits the catheter hub 430 from 360-degree rotation while the catheter hub 430 is installed in the retainer 120.

When the radially extending member points downward (e.g., toward the patient) and generally normal to the bottom surfaces of the retainer 120, the radially extending member extends through the lower opening 150. The hips 270 in the lower opening 150 are spaced sufficiently close to capture the radially extending member in this position and thereby inhibit longitudinal movement of the catheter hub 430.

FIG. 12 is a bottom plan view of an embodiment of the retainer 120 and illustrates that the distance between the first and second mounting wings 210(*a*), 210(*b*) varies in the region of the retainer 120. Width W1 is measured between the first and second mounting wings 210(*a*), 210(*b*) in a lateral direction as shown. Width W2 is measured between the first and second mounting wings 210(*a*), 210(*b*) in a lateral direction as shown.

FIG. 13 is a rear side view of the retainer 120 and further illustrates the widths W1 and W2 from FIG. 12. The first and second mounting wings 210(*a*), 210(*b*) are designed so that width W1 is less than the width W2. Width W1 is selected to deter backward insertion of the medical article into the retainer 120. For example, the width W1 could be selected to be smaller than a spin nut or the connector end of the catheter hub 430. With W1 less than W2, the potential for the medical article being incorrectly inserted into the retainer 120 is reduced.

Medical Articles

Figure 14:
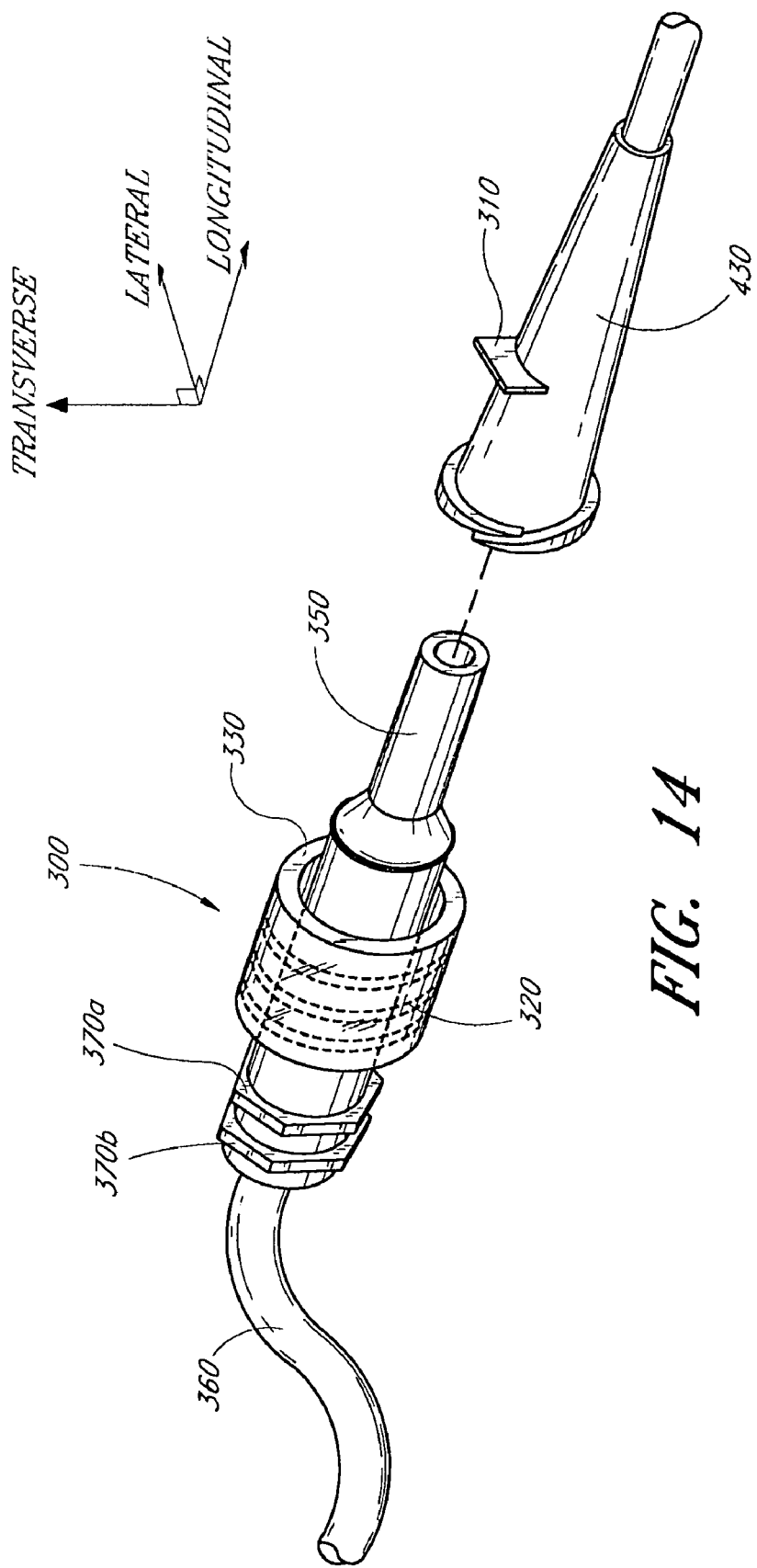
FIG. 14 is a perspective view of an exemplary connector fitting having a spin nut and of a catheter hub with which the securement device of FIG. 1 can be used.

An exemplary medical article for use with the embodiment of the securement device described above will now be described with reference to FIGS. 14 and 15. The medical article can be a single medical article or a combination of one or more medical articles. Such medical articles can be or include, for example, but without limitation, catheters, catheter hubs, catheter adaptors, fluid supply lines, or other similar articles. FIG. 14 is a perspective view of a catheter hub 430 and a connector fitting 300 with a spin nut 330. The connector fitting 300 is disposed upon the end of a medical line 360 which can be connected to a drip bag, blood monitor, or other fluid related medical apparatus.

The connector fitting 300 comprises an elongated body 320 which is attached to the end of the medical line 360. The connector fitting 300 also comprises a portion that is tapered along at least part of its longitudinal length so as to allow the end of this region to fit within the tapered conical portion of a catheter hub 430. The tapered portion 350 of the connector fitting 300 also includes a centrally disposed lumen that communicates with the lumen of the medical line.

Figure 15:
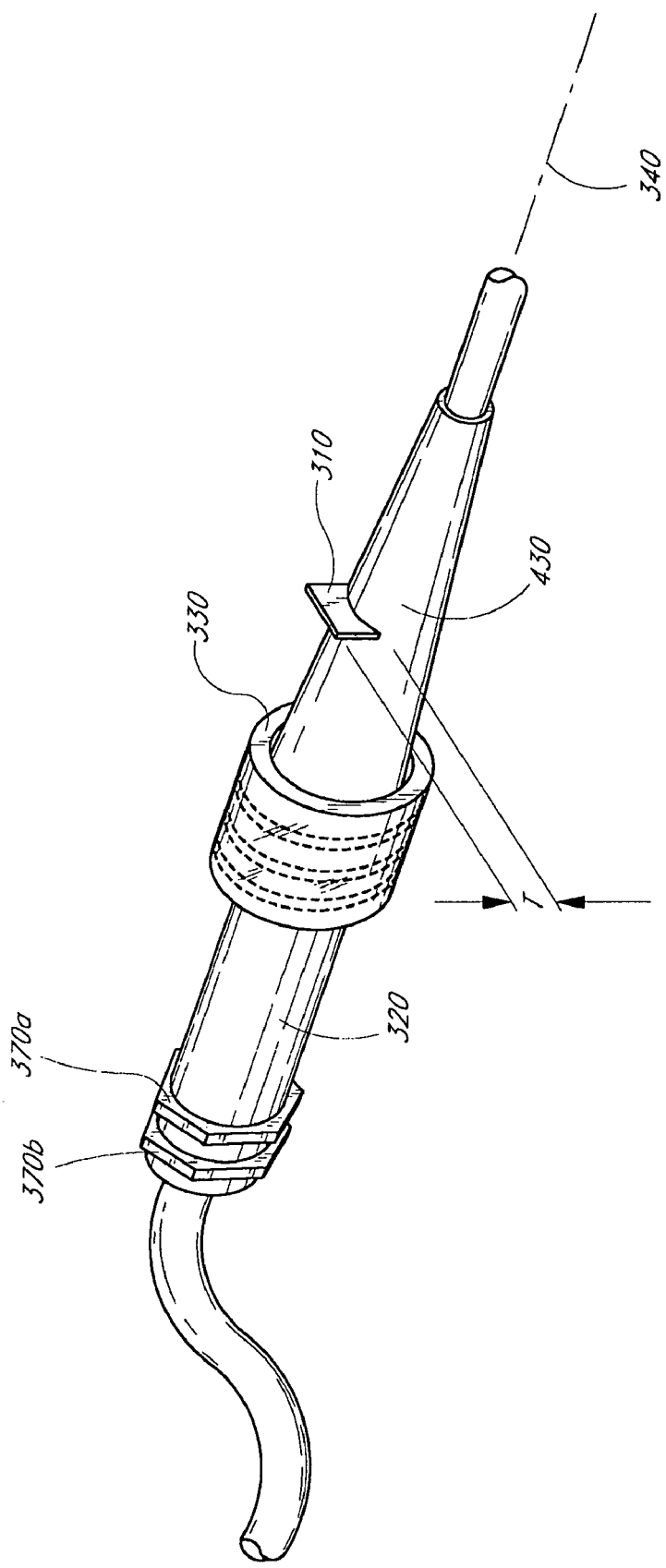
FIG. 15 is a perspective view of the connector fitting of FIG. 14 with the spin nut secured in the forward position and secured to the catheter hub.

FIG. 15 is a perspective view of the connector fitting 300 of FIG. 14 with the spin nut 330 secured in the proximal position and secured to the catheter hub 430. When the connector fitting 300 is inserted into the catheter hub 430, the lumen of the connector fitting is disposed in fluid communication with the lumen of the catheter hub 430. This provides fluid communication between the medical line 360 and the patient.

As seen in FIGS. 14 and 15, the connector fitting 300 has at least two contact surfaces in the form of one radially extending element 370(*a*) disposed upon an end of the elongated body 320 of the connector fitting 300 opposite the tapered end 350. It may be advantageous for the radially extending element 370(*a*) to extend completely around the circumference of the connector fitting 300. Additional contact surfaces in the form of a second radially extending element 370(*b*) can also be disposed upon the elongated body 320, as can additional radial elements (not shown). Those of skill in the art will recognize that the radially extending element or elements 370(*a*) need not have any particular shape or longitudinal thickness. Additionally, the radially extending elements need not have the same shape. For instance, the first radially extending element 370(*a*) can have the hexagonal shape illustrated and the second radially extending element 370(*b*) can have a circular shape.

A spin nut 330 is disposed upon the connector fitting 300 around the elongated body 320 of the fitting. The spin nut 330 is substantially cylindrical in form and is able to move upon the connector fitting 300. The spin nut 330 is capable of both rotational motion around the axis of the connector fitting and axial motion in both the proximal and distal direction along the length of the elongated body 320 of the fitting. The spin nut 330 also includes internal screw threads which are illustrated with phantom lines in FIGS. 14 and 15.

Still referring to FIGS. 14 and 15, a catheter hub 430 includes a body that, in the illustrated embodiment, is configured as a catheter hub 430 and has a generally conical shape and tapers from a large radius to a smaller radius along its length. In the illustrated embodiment, the catheter hub 430 comprises two contact surfaces that together form a radially extending member. The radially extending member can be, for example, a lateral tab 310 which is disposed at a position along the length of the body of the hub. The tab 310 can be gripped by the healthcare provider from the upper side of the retainer 120 in order to immobilize the catheter hub 430 when unscrewing the spin nut 330 or otherwise disengaging the connector fitting 300 from the catheter hub 430. The catheter hub 430 can further include two contact surfaces that together form a longitudinal extending member. The longitudinal extending member is further described below in connection with an additional feature of the securement device 100.

The catheter hub 430 also can include an external screw thread on the outside of the conical body near the end with the larger radius. The screw thread can be used in association with the spin nut 330 of the connector fitting 300 in order to securely interconnect the connector fitting 300 and the catheter hub 430.

With reference to FIG. 11, dimensions L1 and L2 illustrate how the wall 290 described above prohibits 360-degree rotational movement of the catheter hub 430 when the catheter hub 430 is installed in the retainer 120. Referring to FIGS. 11 and 15, when the catheter hub 430 is fully installed in the retainer 120, the push tap 310 extends in a direction away from the central axis 340 of the catheter hub 430 and into the slot 220. As shown in FIG. 15, a maximum distance from the central axis 340 to a distal end of the push tab 310 is distance T. With reference to FIG. 11, to allow the push tab 310 of the catheter hub 430 to rotate in the region of the mounting wing 210(*a*), a distance L1 is selected to be equal to or greater than the distance T. The distance L1 is measured between the axis of the central channel 140 and the top surface of the first mounting wing 210(*a*) as shown in FIG. 11. Selecting L1 to be greater than the distance T permits the push tab 310 to rotate past the first mounting wing 210(*a*).

In contrast, to limit rotation of the catheter hub 430 and push tab 310 in the region of the second mounting wing 210(*b*), a distance L2 is selected to be less than the distance T. The distance L2 is measured between the axis of the central channel 140 and the top surface of the wall 290 as shown in FIG. 11. Selecting L2 to be equal to or less than the distance T does not permit the push tab 310 to rotate past the second mounting wing 210(*b*).

An advantage of limiting the rotation of the catheter adapter 430 when it is installed in the retainer 120 can be understood with reference back to FIG. 14. In FIG. 14, the connector fitting comprises an elongated body 320 which is attached to the end of a medical line. The other end of the elongated body 320 connects to the catheter adapter or hub 430. The push tab 310 is disposed at a position along the length of the body of the hub. The spin nut 330 is disposed around the elongated body 320 of the fitting. Internal screw leads within the spin nut 330 engage with an external screw thread on the catheter hub 430 in order to securely interconnect the connector fitting and the catheter hub 430.

With reference to FIGS. 5 through 13, since the push tab 310 will contact the wall 290 of the retainer 120 when the spin nut 330 is rotated less than 360 degrees, once the push tab 310 contacts the wall 290, the healthcare provider can connect or disconnect the elongated body from the catheter adapter 430 without having to also grip the tab 310. Once the healthcare provider rotates the fitting in either direction so that the tab 310 contacts the wall 290, the catheter hub 430 is effectively immobilized in that direction such that further rotation of the catheter hub 430 in that direction is prohibited. Once immobilized, the healthcare provider can unscrew the spin nut 330 or otherwise disengage the connector fitting from the catheter hub 430 with a single hand. While the use of two hands may be advantageous in certain circumstances when operating the spin nut 330, the retainer 120 allows the healthcare provider to use a single hand.

Similarly, when connecting or re-connecting the elongated body to the catheter hub 430, the healthcare provider can initially rotate the push tab 310, via the spin nut 330, until the push tab 310 contacts the wall 290. Once the push tab 310 contacts the wall 290, the catheter hub 430 is immobilized which can enhance further connecting of the elongated body to the catheter hub 430. In this way, the healthcare provider can continue to turn the spin nut 330 until the spin nut 330 is fully engaged with the catheter hub 430 without having to grip the push tab 310 or catheter hub 430.

The retainer 120 can be used with both luer slip and luer lock connector fittings. The retainer 120 is designed such that even with the push tab 310 positioned in the forward most slot 220, the retainer can fit in the space defined between the push tab 310 and the spin nut 330 with the spin nut 330 fully engaged. The retainer 120 can be further sized to closely fit within this space to provide redundancy in arresting longitudinal movement of the catheter hub 430 relative to the retainer 120. Such slots 220 can also be disposed to extend longitudinally to accommodate radially extending members of greater longitudinal length, such as the splines of a Kipp-style connector. Such splines can be further distributed around the inside circumference of the inverted channel 140 to thereby provide a type of indexing as the longitudinal extending member of the retained medical article engages and disengages each spline while being rotated within the securement device 100 as described below with reference to FIGS. 19 through 23.

Operation

An exemplary process for coupling a medical article with the securement device described above will now be described with reference to FIGS. 16 through 18. A preferred method of using the embodiment illustrated in FIGS. 1-13 will be described in the context of starting an intravenous line. However, the aspects and features of the operational method and the use of the present securement device are not limited to this particular application.

A healthcare provider begins the procedure by inserting an IV catheter into a neonate's vein in a known manner and then attaching an intravenous line to the IV catheter though the luer connection. In particular, the healthcare provider inserts the tapered or luer end 350 of the connector fitting 300 into the catheter hub 430 and then turns the spin nut 330 to thread the spin nut 330 over a thread flange disposed at the distal end of the catheter hub 430. This action draws together the two medical article components and releasably interlocks them. The immediate connection of the IV line to the catheter hub inhibits a back flow of blood through the catheter. The healthcare provider now secures the IV catheter in place on the neonate using the securement device 100. In some variations of this method, however, the securement device 100 can be first be attached to one or both of the medical article (as well as the possibly to the patient) before the healthcare provider makes the connection between the two medical articles.

In order to illustrate more clearly the interaction between the retainer 120 and the catheter hub 430 in this embodiment, the first and second anchor members 110(*a*), 110(*b*) of the securement device 100 are illustrated as detached from the retainer 120. In accordance with the preferred embodiment, however, the entire securement device 100 is assembled in accordance with the above-description (e.g., the mounting wings 210 are attached to the anchor members 110) and is sterilized before use.

Figure 16:
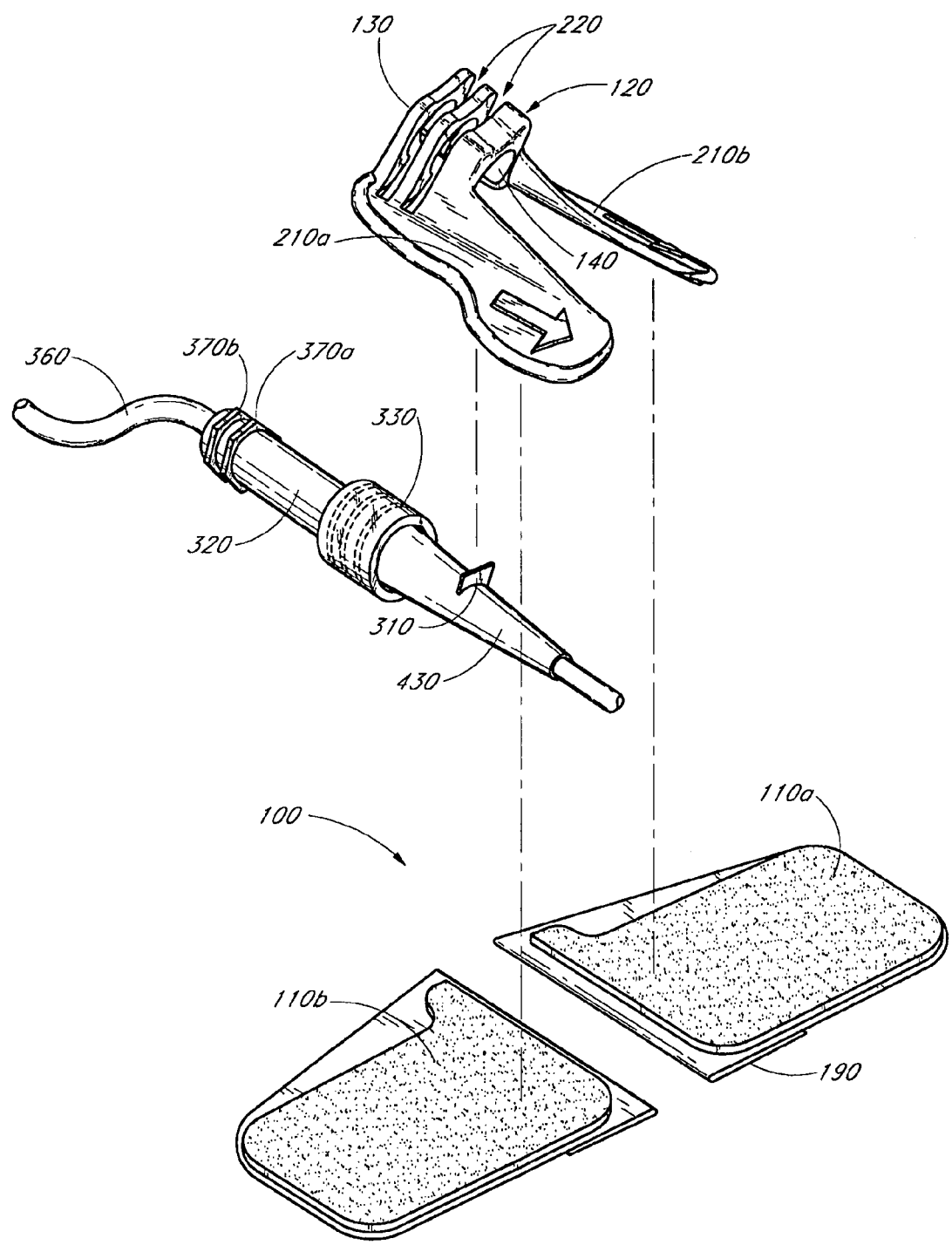
FIG. 16 is an exploded, perspective view of the connector fitting secured to the catheter hub of FIG. 15, both aligned with the first and second anchor members and the retainer of FIG. 1.

FIG. 16 is a perspective view of the connector fitting 300 secured to the catheter hub 430, both aligned with the first and second anchor members 110(*a*), 110(*b*) and the retainer 120. The healthcare provider can secure a medical line 360 and the medical articles to a patient using the above-described securement device 100 or a readily apparent modification thereof. The healthcare provider aligns the central channel 140 of the retainer 120 over the adaptor or catheter hub 430.

Figure 17:
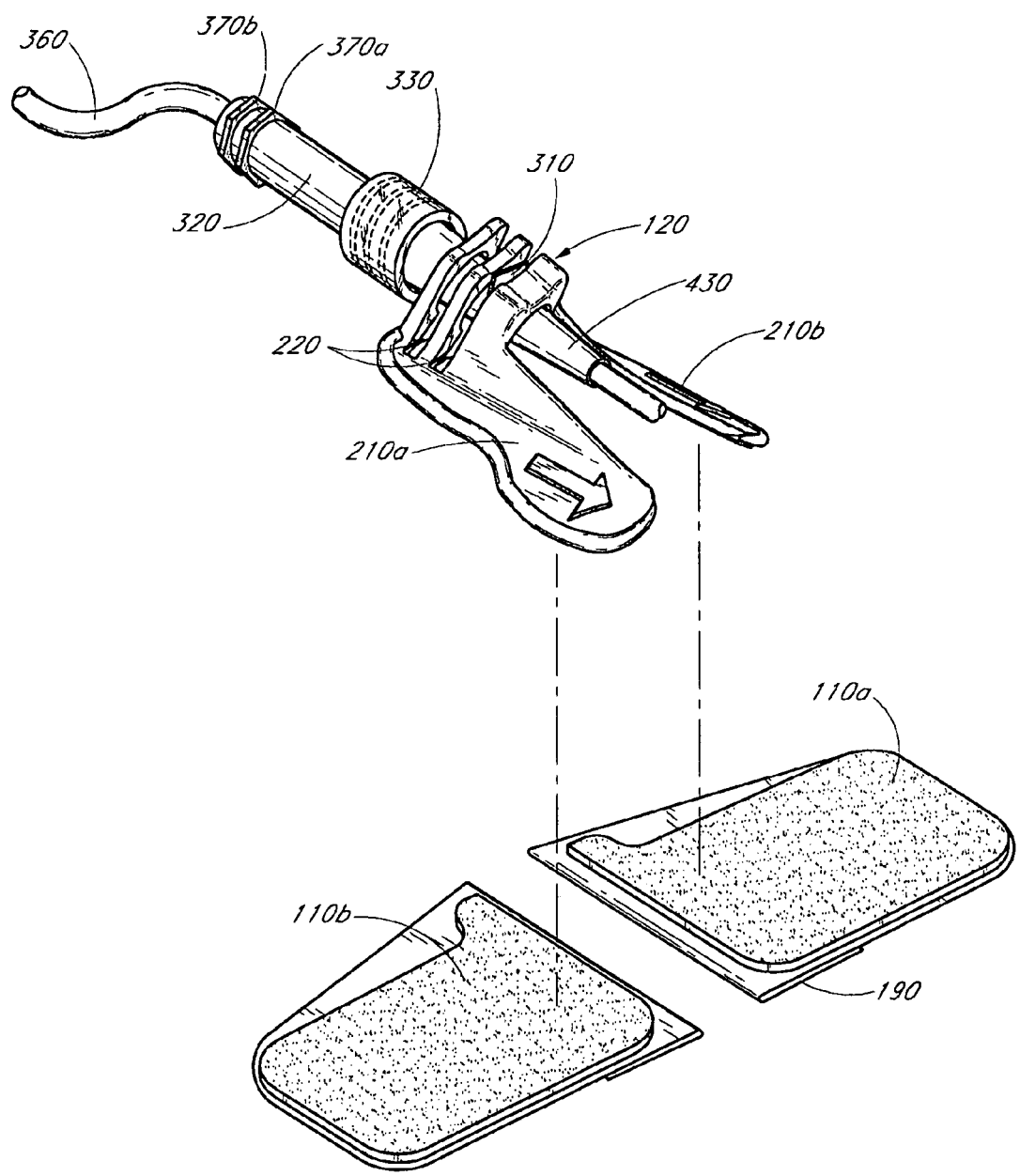
FIG. 17 is an exploded, perspective view of the connector fitting secured to the catheter hub of FIG. 15, with the catheter hub being inserted into the retainer of FIG. 1.

FIG. 17 is a perspective view of the connector fitting 300 secured to the catheter hub 430 with the catheter hub 430 being inserted into the retainer 120. The lower opening 150 in the retainer 120 is pressed over the catheter hub 430 whereby the catheter hub 430 fitting slides into the central channel 140 of the body member 130. Depending on the diameter of the catheter hub 430, the retention surface 165 can provide a snap-fit connection between the hub and the body member 130. The contact surfaces of the catheter hub 430 preferably form one or more radially extending members 310 (e.g., one or more push tabs or annular collars), as shown in the illustrated embodiment. The radially extending member(s) fits into one (or more) of the lateral slots 220 in the retainer. As can be seen, the tab 310 of the catheter hub 430 lies within one of the slots 220 of the retainer 120. In addition, the body of the catheter hub 430 generally lies within the central channel 140 of the retainer. When guided through the lower opening 150 by the healthcare provider, the body of the catheter hub 430 will lie within the central channel 140 of the retainer 120. The abutment surfaces of the slot 220 will inhibit longitudinal migration of the catheter hub 430 through the central channel 140 of the retainer 120. Such slots 220 can also be disposed to extend longitudinally to accommodate radially extending members of greater longitudinal length, such as the splines of a Kipp-style connector as described below with reference to FIGS. 19 through 23.

In addition, if used with a connector fitting 300 in which a portion of the connector fitting, such as the spin nut 330, has a greater radial size than the size of the central channel 140 of the retainer 120, the spin nut 330 can act as a contact surface and will inhibit axial motion in one direction through the central channel 140 of the retainer as well. Using the size of the spin nut 330 or other element having greater radial size than the size of the channel is not required for effective operation of the systems described herein; however, such a technique may be an effective form of securement or redundant securement in some applications.

The combination of the channel shape 140 (both the truncated circular shape and the tapering width), the top portion of the retainer 120, and the interengagement between the slot(s) 220 and the radially extending member(s) 310 on the catheter hub 430 arrest movement of the retained section of the medical line in three dimension: longitudinally, laterally and transversely. Further, the wall 290 in the illustrated embodiment prohibits the catheter hub 430 from 360-degree rotation while the catheter hub 430 is installed in the retainer 120. The rotational stop provided by the wall 290 allows the healthcare provider to attach and detach the spin nut 330 (and thus the connector fitting) to and front the catheter hub 430 without having the remove the catheter hub 430 from the retainer. While this feature is preferred in the illustrated application, it is optional and the wall 290 can be omitted from the securement device, as noted above.

Figure 18:
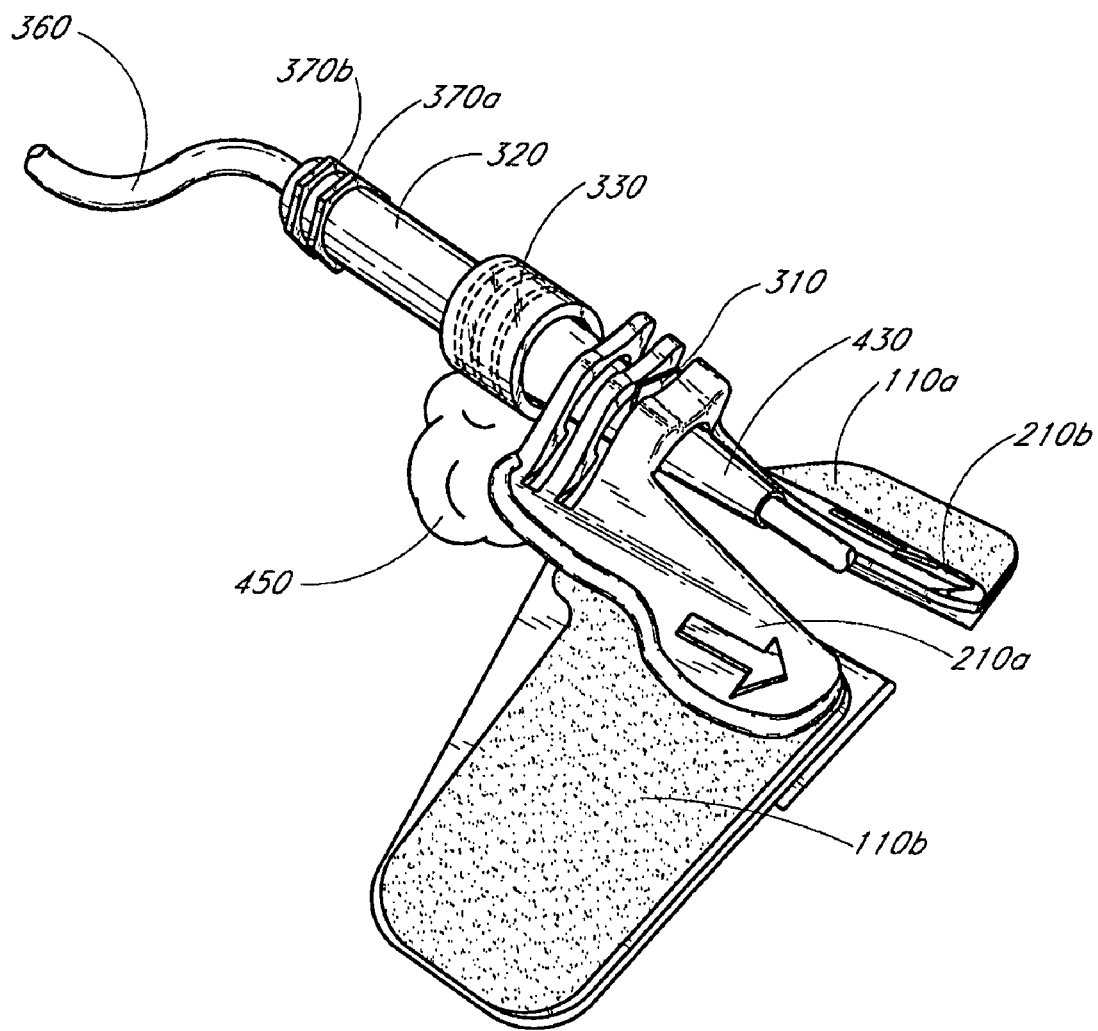
FIG. 18 is a perspective view of the catheter hub secured to the securement device of FIG. 1 with gauze inserted between a distal portion of the retainer and the skin surface of the neonate.

FIG. 18 is a perspective view of the retainer 120 attached to the anchor members 110 and securing the catheter hub 430 therein. Once the catheter hub 430 or other medical article enters the access opening 150 of the retainer 120, the first and second anchor members 110(a), 110(b) are secured to the skin of the neonate such that the attachment portions of the left and right mounting wings 210(a), 210(b) are located above the attachment region 112. The central channel 140 of the retainer surrounds an arc length of more than 180 degrees of the medical article. This inhibits any transverse or lateral motion of the medical article relative to the retainer 120. The catheter hub 430 can be inserted into the retainer either before or after the fitting connector is attached to the hub.

The healthcare provider can first remove one portion of the release liner 180 from the first anchor member 110(a) by gripping the pull tab 190 and pulling the liner 180 away from the lower surface 160 of the first anchor member 110(a). This exposes the adhesive layer of the first anchor member 110(a), which can then be applied to the skin of the neonate near the site where the healthcare provider desires to secure the catheter hub 430 or other medical article. At least parts of the attachment portions 212(a), 212(b) align with at least a portion of the attachment region 112 on the neonate to ensure that the retainer 120 is adequately secured to the neonate. Increasing the amount of the overlap between the attachment portions 212(a), 212(b) and the attachment region 112 enhances securement to the neonate. As explained above, when the length of the attachment region 112 on the neonate is less than the overall length of the retainer 120 or has a longitudinal curvature that prevents the entire retainer 120 from contacting the skin of the neonate, a distal portion of the retainer 120 may be elevated from the surface of the neonate. In such instances, a soft material 450, for example, cotton or gauze can be inserted between the surface of the neonate and the elevated distal portion of the retainer 120 to thereby further inhibit transverse motion or rocking of the retainer 120 upon the skin.

The adhesive layer of the second anchor member 10(b) can be similarly exposed. The remainder of the release liner 180 for the first and second anchor members 110(a), 110(b) can then be removed and the anchor members 110(a), 110(b) attached to the skin of the neonate. As a variation, the release liner 180 on one anchor member can be pulled away and the anchor member can be fully attached to the patient before attaching the second anchor member to the patient.

Additional Embodiments

Figure 20:
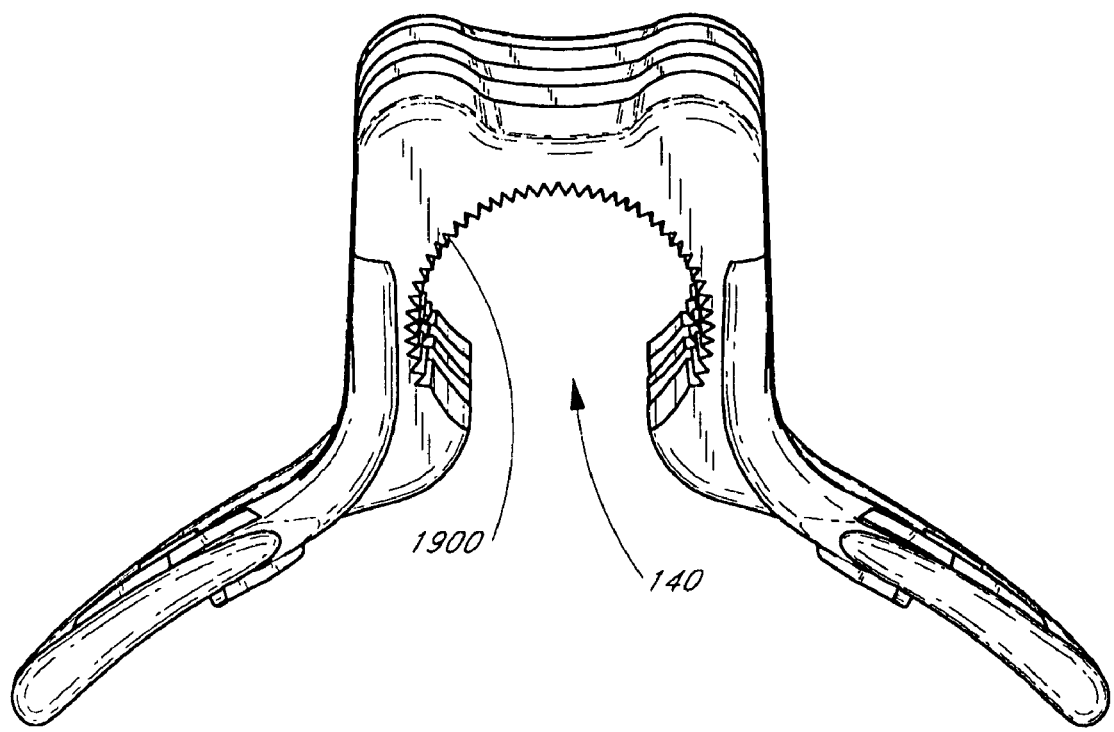
FIG. 20 is a front side view of the retainer of FIG. 19.

FIG. 19 is a perspective view of a retainer having splines 1900 distributed around the inside of the inverted channel 140 for engaging and disengaging with a longitudinal extending member of the retained medical article. The inverted channel 140 of the retainer captures or receives a longitudinally extending spline 1900 on the medical article. FIG. 20 is a front side view of the retainer from FIG. 19 showing the longitudinally extending splines 1900.

Figure 21:
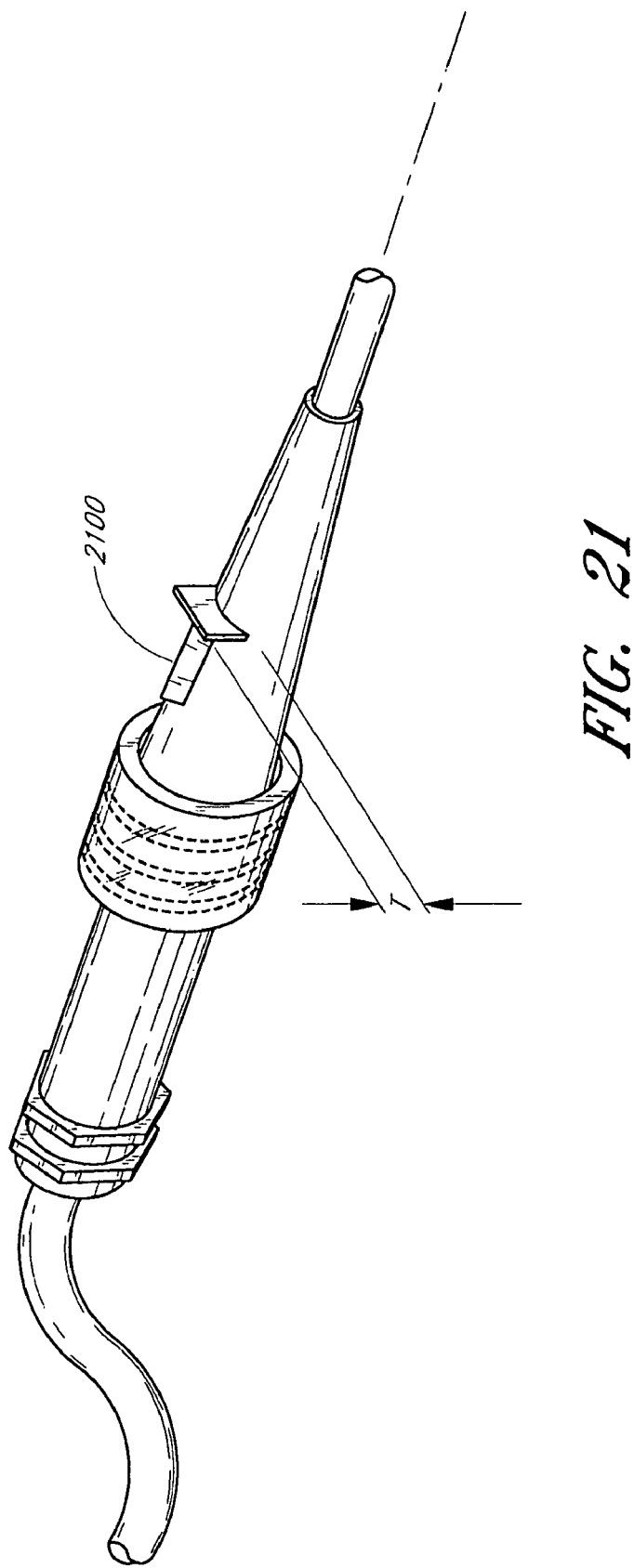
FIG. 21 is a perspective view of a connector fitting secured to a catheter hub having a longitudinal extending member for engaging with the splines on the retainer of FIG. 19.
Figure 22:
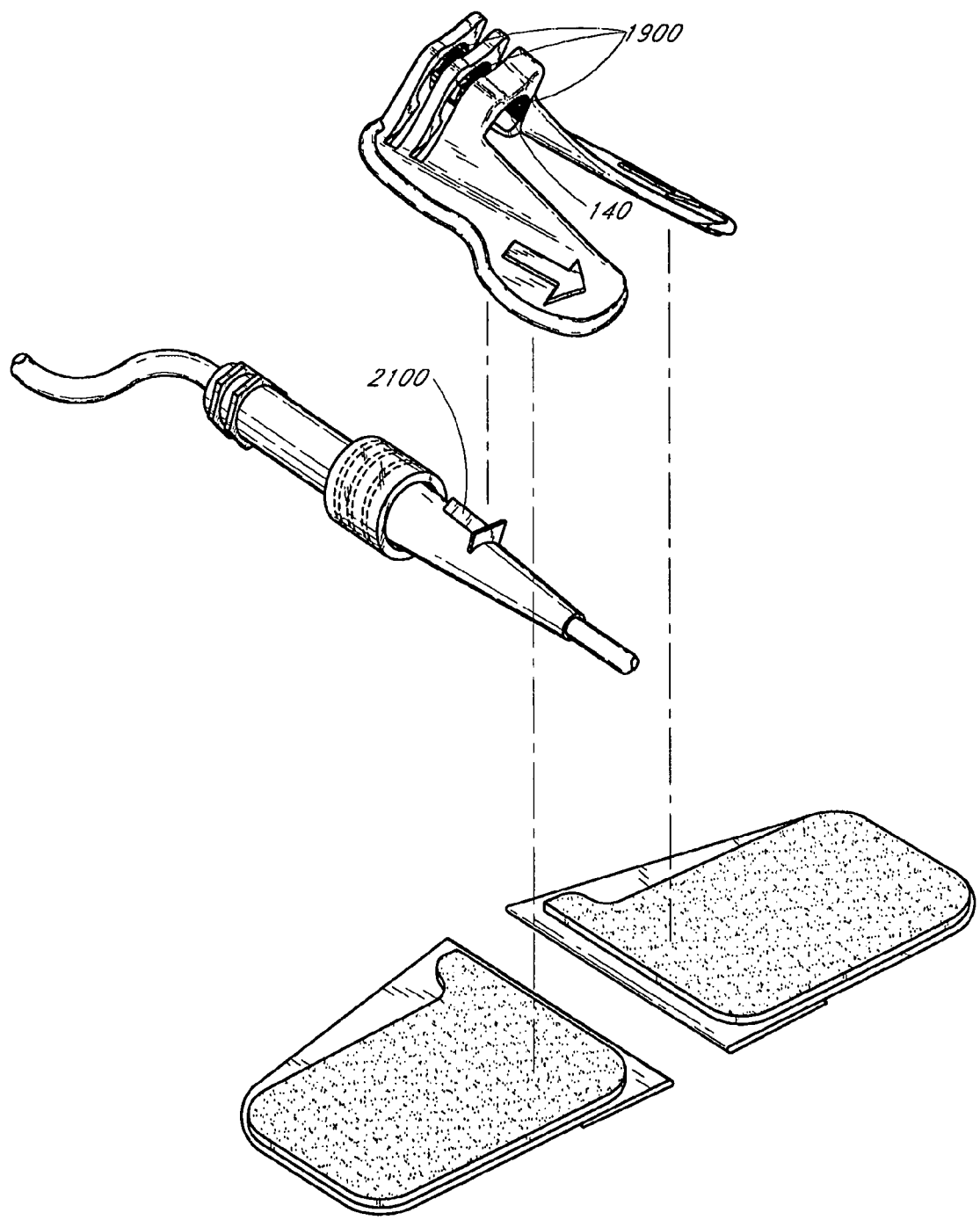
FIG. 22 is an exploded, perspective view of the connector fitting secured to the catheter hub of FIG. 21, both aligned with the first and second anchor members and the retainer of FIG. 19.
Figure 23:
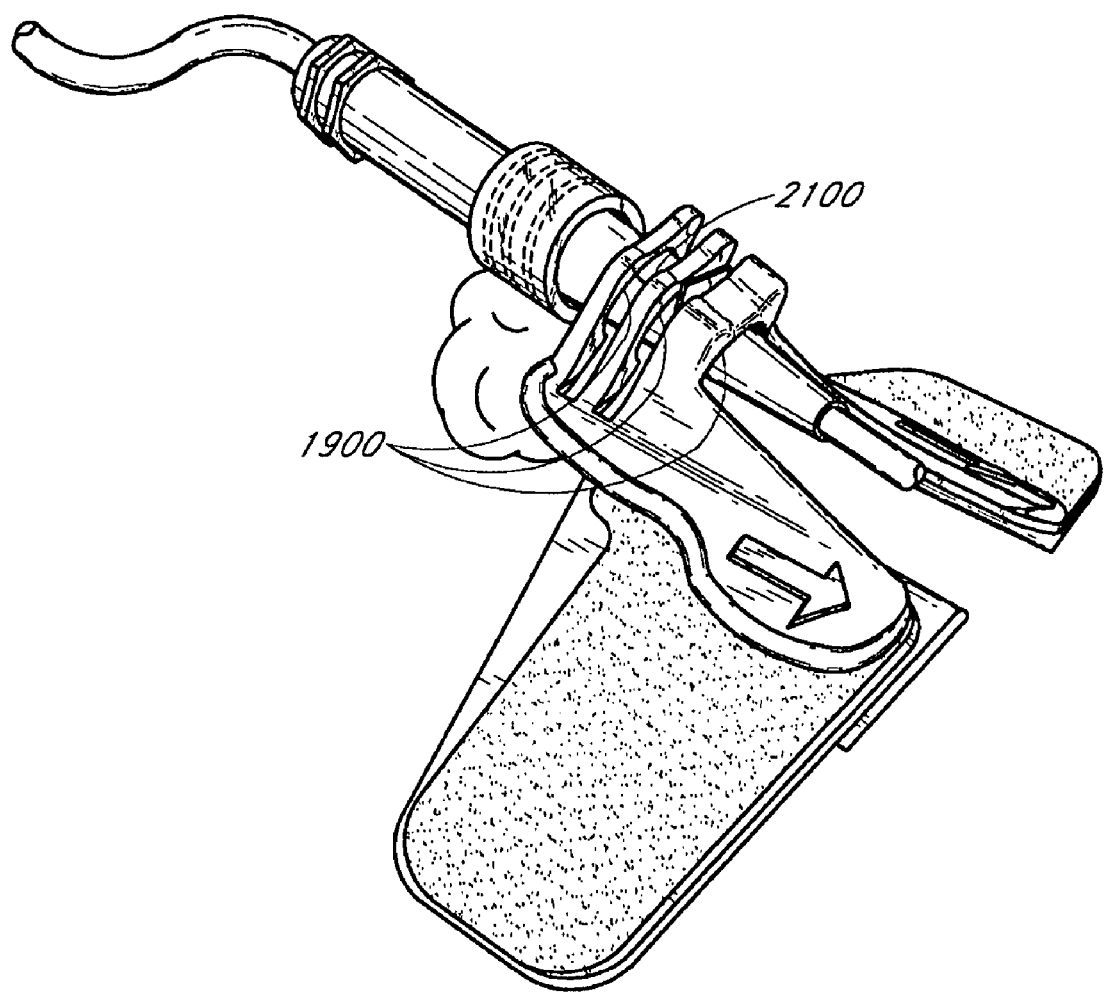
FIG. 23 is a perspective view of the catheter hub secured to the securement device of FIG. 19 with the longitudinal extending member engaged with the splines on the inside of the retainer.

FIG. 21 is a perspective view of a medical article having a longitudinal extending member 2100 for engaging with the splines 1900 on the retainer of FIG. 19. As illustrated in FIGS. 19 through 23, the splines 1900 can be distributed around the inside circumference of the inverted channel 140 to thereby provide a type of indexing as the longitudinal extending member 2100 (see FIG. 21) engages and disengages each spline 1900 as the medical article is rotated within the retainer. FIG. 23 is a perspective view of the medical article secured to the retainer of FIG. 19 with the longitudinal extending member 2100 engaged with the splines 1900 on the inside circumference of the inverted channel 140. Such a construction can provide a form of indexing as the retained medical article is rotated within the inverted channel 140.

As understood from the above description of the securement device embodiment shown in FIGS. 1-13 and 16-18, the securement device 100 attaches to a region on a neonate that can be smaller than the footprint of the securement device since substantial portions of the mounting feet 210(a), 210(b) or attachment portions 212(a), 212(b) are offset from the body member 130 of the retainer 120. In this way, the body member 130 grips the medical article at a longitudinal location near to, or outside of, the attachment region 112 while the offset mounting feet 210(*a*), 210(*b*) are disposed over the attachment region 112.

The securement device further arrests longitudinal movement of the retained section of the catheter hub 430 by interacting with at least one and preferably two contact surfaces of the push tab 310, which constitutes a radially extending member in the illustrated embodiment. This approach for arresting longitudinal movement can also be used with other types of radially extending members or contacts (e.g., contact surfaces) on the catheter hub 430 or other medical articles or components thereof.

In other embodiments, the retainer can be configured to fit between contacts on a medical article or medical articles. For example, the retainer can be sized to fit between the proximal side of the spin nut 330 and the distal side of the push tab 310. In such a case, the end surfaces of the retainer function as the abutment surfaces and cooperate with adjacent contacts on the medical article(s). Additionally, the retainer can be configured to not only fit between two contacts on the medical article(s) but also can be configured to receive one or more radially extending members of the medical article(s).

In a variation of this approach, longitudinal movement can also be fully arrested (i.e., arrested in both directions along the longitudinal axis) by (1) the interaction of an abutment on the retainer and a distally facing contact in combination with (2) the shape of the channel 140. For example, in the embodiment described with reference to FIG. 5, the tapering shape of the channel 140, which decreased in size in the proximal direction, inhibited longitudinal movement toward the insertion site. The interaction between a proximal side wall of the slot 220 and the distal side of the push tab 310 prevents longitudinal movement in the distal direction. Thus, some embodiments need only include one abutment. As noted above, the channel 140 can have a tapering shape along at least a portion of its length and a step down in diameter along its length. The tapering shape can arrest longitudinal movement in one direction and an abutment, which is formed at the diameter step down, can interact with a corresponding contact (e.g., contact surface) on the medical article to arrest longitudinal movement in the opposite direction.

The various embodiments of securement devices and techniques described above thus provide a number of ways to provide safe and releasable securement for medical articles to the skin of a patient. In addition, the techniques described may be broadly applied for use with a variety of medical lines and medical procedures.

Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein. In addition to the variations described herein, other known equivalents for each feature can be incorporated by one of ordinary skill in this art to construct anchoring systems in accordance with principles of the present invention.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In particular, while the present retainer has been described in the context of particularly preferred embodiments, the skilled artisan will appreciate, in view of the present disclosure, that certain advantages, features and aspects of the retainer may be realized in a variety of other applications, many of which have been noted above. For example, while particularly useful for small-scale applications, such as the illustrated medical application, the skilled artisan can readily adopt the principles and advantages described herein to a variety of other applications, including larger scale devices. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the present invention herein disclosed should not be limited by the particular disclosed embodiments described above, but should be determined only by a fair reading of the claims that follow.

What is claimed is:

1. A securement device for anchoring a medical article to an attachment region on a neonate's skin, the securement device comprising:
   at least one anchor member having a lower adhesive surface configured to attach to skin of the neonate; and
   a retainer comprising,
      a body member having a channel formed therethrough about a channel axis and terminating at a proximal end of the body member, the channel having a longitudinal access opening to allow at least ingress of a portion of the medical article into the channel, the longitudinal access opening extending the entire length of the body member and being disposed on an underside of the body member, the channel having a surface that extends through an arc of greater than 180 degrees so as to elevate the portion of the medical article above the skin of the neonate,
      at least one abutment extending generally normal to the channel axis so as to inhibit longitudinal movement of the retained portion of the medical article relative to the body member, and
      at least one mounting wing supporting the body member and having an attachment portion disposed on a bottom surface of the at least one mounting wing, the attachment portion being mounted on the anchor member and directly above the attachment region on the neonate's skin at least when the at least one anchor member is attached to the skin, the attachment portion being disposed entirely to a proximal side of and beyond the proximal end of the body member, the attachment portion being laterally offset from the body so as to not block ingress of the portion of the medical article into any portion of the channel from a location below the at least one anchor member,
      wherein a portion of the bottom surface distal to the attachment portion is disposed at least below the body member and outside the attachment region on the neonate's skin at least when the at least one anchor member is attached to the skin.

2. A securement device as in claim 1, wherein the mounting wing includes a support arm that extends from the body member in a proximal direction and links the body member to the attachment portion.

3. A securement device as in claim 1, wherein a distal portion of the mounting wing is elevated relative to the attachment portion.

4. A securement device as in claim 1, wherein the at least one abutment is located between the proximal end and a distal end of the body member along the axis of the channel.

5. A securement device as in claim 1, wherein the at least one mounting wing supports at least a portion of the body member at a position elevated relative to at least a portion of the attachment portion.

6. A securement device as in claim 1, wherein a substantial portion of the at least one mounting wing extends from the body member in a proximal direction.

7. A securement device as in claim 1, wherein the channel has a shape generally corresponding to a frustoconical shape of a catheter hub, and a distance between a proximal end of the at least one each mounting wing and the at least one abutment substantially equals a distance between a proximal end of the catheter hub and a radially extending member on the catheter hub.

8. A securement device as in claim 1, wherein the channel has a tapering shape.

9. A securement device as in claim 1, wherein the retainer comprises another abutment disposed such that the abutments at least substantially oppose each other.

10. A securement device as in claim 1, wherein the channel axis is aligned with the skin of the patient at an angle of approximately 7 degrees when the at least one anchor member is attached to the skin.

11. A securement device as in claim 1, wherein the channel axis is aligned with the skin of the patient at an angle of approximately 12.5 degrees when the at least one anchor member is attached to the skin.

12. A securement device for anchoring a medical article to a patient's skin, the securement device comprising:
    an anchor member; and
    a retainer comprising
        a body member including a channel formed therethrough, the channel retaining a portion of the medical article and having a longitudinal access opening disposed on an underside of the body member to allow ingress of the medical article into the channel,
        at least one abutment extending generally normal to an axis of the channel to inhibit longitudinal movement of the medical article, and
        at least one mounting wing supporting the body and having an attachment portion mounted to the anchor member, the attachment portion being configured to contact the anchor member directly above the patient's skin, an overall longitudinal length of the at least one mounting wing exceeding the longitudinal length of the attachment portion so that at least a portion of the mounting wing facing the patient's skin does not contact the patient's skin and does not contact the anchor member, an overall lateral width of the at least one mounting wing being less than a lateral distance from the axis to an outer extremity of the retainer so as to not block ingress of the medical article into the channel from a location below the retainer.

13. A securement device as in claim 12, wherein the mounting wing extends proximally from the body member from a location on the body member near the access opening.

14. A securement device as in claim 12, wherein the attachment portion of the mounting wing is disposed entirely to one side of and beyond a proximal end of the body member.

15. A securement device as in claim 12, wherein the at least one mounting wing includes a support arm that extends from the body member in a proximal direction and links the body member to the attachment portion.

16. A securement device as in claim 12, wherein a distal portion of the at least one mounting wing is elevated relative to the attachment portion.

17. A securement device as in claim 12, wherein the at least one abutment is located between a proximal end and a distal end of the body member along the axis of the channel.

18. A securement device as in claim 12, wherein the at least one mounting wing supports at least a portion of the body member at a position elevated relative to at least a portion of the attachment portion.

19. A securement device as in claim 12, wherein a substantial portion of the at least one mounting wing extends from the body member in a proximal direction.

20. A securement device as in claim 12, wherein the channel has a shape generally corresponding to a frustoconical shape of a catheter hub, and a distance between a proximal end of the at least one mounting wing and the at least one abutment substantially equals a distance between a proximal end of the catheter hub and a radially extending member on the catheter hub.

21. A securement device as in claim 12, wherein the channel has a tapering shape.

22. A securement device as in claim 12, wherein the retainer comprises another abutment disposed such that the abutments at least substantially oppose each other.

23. A securement device as in claim 12, wherein the channel axis is aligned with the skin of the patient at an angle of approximately 7 degrees when the anchor member is attached to the skin.

24. A securement device as in claim 12, wherein the channel axis is aligned with the skin of the patient at an angle of approximately 12.5 degrees when the anchor member is attached to the skin.

* * * * *

UNITED STATES PATENT AND TRADEMARK OFFICE
CERTIFICATE OF CORRECTION

| | |
|---|---|
| PATENT NO. | : 8,057,440 B2 |
| APPLICATION NO. | : 11/442701 |
| DATED | : November 15, 2011 |
| INVENTOR(S) | : Steven F. Bierman |

Page 1 of 1

It is certified that error appears in the above-identified patent and that said Letters Patent is hereby corrected as shown below:

At Page 1 (Item 73) Assignee, Line 1, Change "Venectec" to --Venetec--.

At Column 1, Line 27, Change "babies'present" to --babies' present--.

At Column 1, Line 32, Change "(IV)" to --IV--.

At Column 6, Line 8, After "use" insert --with--.

At Column 6, Line 23, Change "abutment" to --abutments--.

At Column 6, Line 40, Change "retainer" to --retainer,--.

At Column 6, Line 47, Change "attachments" to --attachment--.

At Column 18, Line 50, Change "direction" to --directions--.

At Column 22, Line 26, Change "10(b)" to --110(b)--.

At Column 25, Line 11, In Claim 7, after "one" delete "each".

Signed and Sealed this
Seventeenth Day of July, 2012

David J. Kappos
*Director of the United States Patent and Trademark Office*